US006617315B1

(12) United States Patent
Chamberlain et al.

(10) Patent No.: US 6,617,315 B1
(45) Date of Patent: Sep. 9, 2003

(54) THERAPEUTIC COMPOUNDS

(76) Inventors: Stanley Dawes Chamberlain, Glaxo Wellcome Inc., Five Moore Dr., P.O. Box 13398, Chapel Hill, NC (US) 27709; George Walter Koszalka, Glaxo Wellcome Inc., Five Moore Dr., P.O. Box 13398, Chapel Hill, NC (US) 27709; Jeffrey H. Tidwell, Glaxo Wellcome Inc., Five Moore Dr., P.O. Box 13398, Raleigh, NC (US) 27709; Nanine Agneta Vandraanen, 3038 Shadow Hill Cir., Thousand Oaks, CA (US) 91360

( * ) Notice: Subject to any disclaimer, the term of this patent is extended or adjusted under 35 U.S.C. 154(b) by 0 days.

(21) Appl. No.: 09/712,739

(22) Filed: Nov. 14, 2000

Related U.S. Application Data

(63) Continuation of application No. 90/101,103, filed as application No. PCT/GB96/03151 on Dec. 19, 1996, now Pat. No. 6,204,249.

(30) Foreign Application Priority Data

Jan. 5, 1996 (GB) .............................................. 9600143

(51) Int. Cl.$^7$ .............................................. C07H 17/02
(52) U.S. Cl. ........................ 514/43; 514/394; 536/28.9
(58) Field of Search ................... 514/43, 394; 536/28.9

(56) References Cited

U.S. PATENT DOCUMENTS

| 3,399,987 A | 9/1968 | Woods |
| 3,555,040 A | 1/1971 | Frick |
| 3,655,901 A | 4/1972 | Jensen |
| 4,002,623 A | 1/1977 | Kadin |
| 5,248,672 A | 9/1993 | Townsend |
| 5,360,795 A | 11/1994 | Townsend |
| 5,399,580 A | 3/1995 | Daluge |
| 5,473,063 A | 12/1995 | Classon |
| 5,534,535 A | 7/1996 | Townsend |
| 5,574,058 A | 11/1996 | Townsend |
| 5,646,125 A | 7/1997 | Townsend |
| 5,654,283 A | 8/1997 | Townsend |
| 5,665,709 A | 9/1997 | Townsend |
| 5,874,413 A | 2/1999 | Townsend et al. |
| 5,955,610 A | 9/1999 | Nguyen-Ba et al. |
| 6,204,249 B1 * | 3/2001 | Chamberlain et al. ........ 514/43 |

FOREIGN PATENT DOCUMENTS

| DE | A2 130 030 | 12/1972 |
| EP | 0 136 938 | 4/1985 |
| EP | A 0 304624 | 3/1989 |
| EP | 0 350 467 | 1/1990 |
| EP | 0 515 156 | 11/1992 |
| WO | WO A92 07867 | 5/1992 |
| WO | 92/18517 | 10/1992 |
| WO | 93/18009 | 9/1993 |
| WO | WO94/08456 | 4/1994 |
| WO | 96/01833 | 1/1996 |

OTHER PUBLICATIONS

Gosselin et al., "Synthesis and biological evaluation of new 5,6–dichlorobenzimidazole nucleoside derivatives," Antiviral Chem. Chemotherapy, vol. 5, pp. 243–256 (1994).

Revankar et al., The synthesis of 2–chloro–1–(β–D–ribofuranosyl)benzimidazole and certain related derivatives (1), J. Heterocycles, vol. 5, pp. 477–483 (1968).

Revankar et al., The synthesis of 2–chloro–1–β–D–ribofuranosyl–5,6–dimethylbenzimidazole and certain related derivatives (1), J. Heterocycles, vol. 5, No. 4, pp. 615–620 (1968).

Gordon et al., "Kinetics of Decay in the Expression of Interferon–Dependent mRNAs Responsible for Resistance to Virus," Proc. Acad. Sci. USA, 77(1) pp. 452–456 (1980).

Devivar et al., "Benzimidazole Ribonucleosides: Observation of an Unexpected Nitration When Performing Non–Aqueous Diazotizations with t–butyl Nitrite," Biorganic Et Medicinal Chem. Letters, 2(9), pp. 1105–1110 (Sep. 1992).

Tiggers et a., "Human CD8+ Herpes Simplex Virus–Specific Cytotoxic T–Lymphocyte Clones Recognize Diverse Viron Protein Antigens," J. Virology, 66(3), PP. 1622–1634 (1992).

Devivar et al., "Benzimidazole Ribonucleosides: Design, Synthesis, and Antiviral Activity of Certain 2–(Alkylthio-)–and 2–(Benzylthio)–5,6–dichloro–1–( α–D–ribofuranosyl)benzimidazoles," J. Med. Chem. 37(18), pp. 2942–2949 (Sep. 1994).

Townsend et al., "Design, Synthesis and Antiviral Activity of Certain 2,5,6–Trihalo–1–(α–D–ribofuranosyl)benzimidazoles," J. Med. Chem. 38(20), pp. 4098–4105 (Sep. 1995).

Yankulov et al., "The Transcriptional Elongation Inhibitor 5,6–Dichloro–1–α–D–ribofuranosylbenzimidazole Inhibits Translation Factor IIH–Associated Protein Kinase," J. Biol. Chem., 270(41), pp. 23922–23925 (Oct. 1995).

Nassiri et al., "Comparison of Benzimidazole Nucleosides and Ganciclovir on the In Vitro Proliferation and Colony Formation of Human Bone Marrow Progenitor Cells," British J. Haematology, 93(2), pp. 273–279 (May 1996).

Gundmundsson et al., "Synthesis and Antiviral of Certain 5'–Modified Analogs of 2,5, 6–Trichloro–1–(α–D–ribofuranosyl)benzimidazole," J. Med. Chem. 40(5), pp. 785–793 (Feb. 1997).

Zou et al., "Design, Synthesis, and Antiviral Evaluation of 2–Chloro–5,6–dihalo–1–( α–D–ribofuranosyl)benzimidazoles as Potential Agents for Human Cytomegalovirus Infections," J. Med. Chem. 40(5), pp. 811–818 (Feb. 1997).

Physician's Desk Reference, 52nd Ed., Arky and Sifton (eds.), Medical Economics Co., Montvale, NJ, 1998, pp. 2452–2454 (see "Cytovene").

(List continued on next page.)

Primary Examiner—James O. Wilson
Assistant Examiner—La Tonia M. Fisher

(57) ABSTRACT

The present invention relates to benzimidazole derivatives and their use in medical therapy particularly for the treatment or prophylaxis of restenosis.

5 Claims, No Drawings

OTHER PUBLICATIONS

TheE Merck Index, 11th Ed., Budavari et al., (eds.) Merck Et Co., Rahway, NJ, 1989, p. 682.

Methods of Nucleoside Synthesis Vorbrueggen, Helmut. Res. Lab., Schering A.–G., Berlin, D–1000/65, Fed. Rep. Ger. NATO Adv. Study Inst. Ser., Ser. A (1979), A26(Nucleoside Analogues: Chem., Biol., Med. Appl.), 35–69.

Vorbrüggen et al., "Nucleoside Synthesis with Trimethylsilyl Triflate and Perchlorate as Catalysts," Chem. Ber. 114, pp. 1234–1255 (1981).

Vorbrüggen et al., "New Catalysts for the Synthesis of Nucleosides," Angew. Chem. Internat. Edit. 14(6), pp. 421–422 (1974).

Meggio et al., *European Journal of Biochemistry*, vol. 187, No. 1, Jan. 1990, pp. 89–94, "Ribofuranosyl–benzimidazole derivatives as inhibitors of casein kinase–2 and casein kinase–1".

Oivanen et al., *Nucleosides Et Nucleotides*, vol. 8, No. 1, 1989, pp. 133–144, "Mechanism for a cid–catalyzed hydrolysis sof nucleoside and acyclunocleoside analogues of benzimidazole".

Bucknall, R.A., *Journal Gen. Virology*, vol. 1, 1967, pp. 89–99, "The effects of substituted benzimidazoles on the growth of viruses and the nucleic acid metabolism of host cells".

Dobrowolska, et al., *Biochimica Et Biophysica ACTA*, vol. 1080, No. 3, Nov. 15, 1991, pp. 221–226, "benzimidazole Nucleoside Analogues As Inhibitors of Plant (Maze Seedlings) Casein Kinases".

Seela et al., *Helvetica Chimica ACTA*, vol. 79, Mar. 20, 1996, pp. 488–498, "Synthesis of 4–substituted 1H–benzimidazole 2'–deoxyribonucleosides and utility of the 4–nitro compound as universal base".

Dawson et al., *Phytopathology*, vol. 77, No. 3, 1987, pp. 477–480, "Modifications of nucleic acid precusosrs that inhibit plant virus modification".

* cited by examiner

THERAPEUTIC COMPOUNDS

This application is filed pursuant to 35 U.S.C. §120, as a continuation of U.S. patent application Ser. No. 09/101,103, filed Jul. 13, 1998 now U.S. Pat. No. 6,204,249, which was filed pursuant to 35 U.S.C. §371 as a United States National Phase Application of International Application No. PCT/GB96/03151 filed Dec. 19, 1996, which claims priority from GB 9600143.3, filed Jan. 5, 1996.

The present invention relates to benzimidazole derivatives and their use in medical therapy particularly for the treatment or prophylaxis of virus infections such as those caused by herpes viruses. The invention also relates to the preparation of the benzimidazole derivatives and pharmaceutical formulations containing them.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6) and human herpes virus type 7 (HHV-7). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal.

VZV is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin-cell lymphoma, thymomas and oral hairy leukoplakia. EBV infections have also been found in association with a variety of epithelial-cell-derived tumours of the upper and lower respiratory tracts including the lung.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of worldwide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

PCT Patent Specification Nos. WO 92/07867 and WO 94/08456 describe certain antiviral polysubstituted benzimidazole nucleoside analogues including -D-ribofuranosyl riboside analogues. PCT Patent Specification No. WO 93/18009 describes certain antiviral benzimidazole analogues in which the sugar residue is replaced by a carbocyclic group.

It has now been discovered that certain L-sugar substituted benzimidazole compounds as referred to below, are useful for the treatment or prophylaxis of certain viral infections. According to a first aspect of the present invention, novel compounds of the formula (I) are provided:

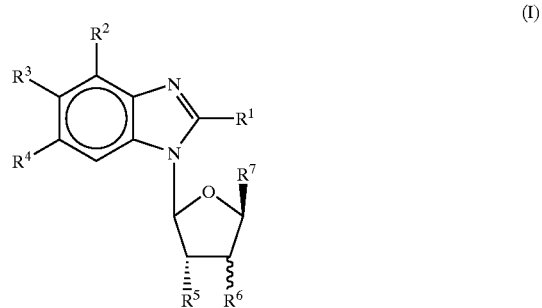

(I)

wherein;

$R^1$ represents hydrogen, a halo atom or azido;
—$NR^8R^9$ where $R^8$ and $R^9$, which may be the same or different, are each independently selected from hydrogen, hydroxyl, $C_{1-12}$ alkyl, for example $C_{1-6}$ alkyl (where the alkyl moiety may be optionally substituted by one or more substituents selected from halo, amino, azido, hydroxy, cyano, $NO_2$, $NHR^{10}$, $SO_2R^{10}$, $SR^{10}$, $OR^{10}$, $COR^{10}$ and halo$C_{1-6}$ alkyl where $R^{10}$ is $C_{1-6}$ alkyl, $C_{3-6}$ alkenyl, $C_{2-6}$ alkynyl, or aryl), $C_{2-8}$ alkenyl, $C_{1-6}$ alkoxy, $C_{3-7}$ cycloalkyl, $C_{2-8}$ alkynyl, $C_{3-7}$ cycloalkenyl, $C_{3-7}$ cycloalkyl$C_{1-6}$ alkyl, aryl, aryl$C_{1-6}$ alkyl, heteroaryl, heteroaryl$C_{1-6}$ alkyl, heterocyclyl and heterocyclyl$C_{1-6}$ alkyl, or $R^8R^9$ together with the N atom to which they are attached form a 3,4,5 or 6 membered heterocyclic ring;

—NHNR$^{11}$R$^{12}$ where R$^{11}$ and R$^{12}$, which may be the same or different, each represent hydrogen or C$_{1-6}$ alkyl;

—N=NC$_{1-6}$ alkyl or —NHOC$_{1-6}$alkyl;

R$^2$ represents hydrogen, halo atom, C$_{1-6}$alkyl or C$_{2-6}$alkenyl;

R$^3$ and R$^4$, which may be the same of different, each represent hydrogen, halogen or NO$_2$;

R$^5$ and R$^6$, which may be the same or different, each represent hydrogen or hydroxy;

R$^7$ represents hydrogen, CH$_3$ or CH$_2$R$^{13}$ where R$^{13}$ may be selected from hydroxy, a halo atom and OR$^{14}$ (where R$^{14}$ is hydrogen, C$_{1-8}$alkyl, aryl or arylC$_{1-6}$alkyl);

with the proviso that when R$^2$ represents hydrogen, R$^3$ and R$^4$ each represent chloro, R$^5$ and R$^6$ represent an erythro hydroxy group and R$^7$ is —CH$_2$OH then R$^1$ represents azido, —NR$^8$R$^9$ where R$^8$ and R$^9$, which may be the same or different, are each independently selected from hydroxyl, C$_{1-6}$ alkyl (where the alkyl moiety is substituted by one or more substituents selected from amino, azido, NO$_2$, NHR$^{10}$, SO$_2$R$_{10}$, SR$^{10}$, OR$^{10}$, haloC$_{1-6}$ alkyl where R$^{10}$ is as hereinbefore defined), C$_{7-12}$ alkyl (where the alkyl moiety is optionally substituted by one or more substituents selected from halo, amino, azido, hydroxy, cyano, NO$_2$, NHR$^{10}$, SO$_2$R$^{10}$ SR$^{10}$, OR$^{10}$, COR$^{10}$ and haloC$_{1-6}$ alkyl where R$^{10}$ is as hereinbefore defined), C$_{1-6}$ alkoxy, C$_{3-7}$ cycloalkenyl, heteroaryl, heteroaryl C$_{1-6}$ alkyl and heterocyclyl;

—NHNR$^{11}$R$^{12}$ where R$^{11}$ and R$^{12}$ are as hereinbefore defined;

—N=NC$_{1-6}$ alkyl or —NHOC$_{1-6}$ alkyl;

or a pharmaceutically acceptable derivative thereof.

The present invention further provides compounds of formula (I) wherein the sugar moiety is selected from the following:

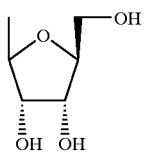

a

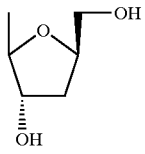

b

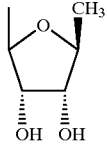

c

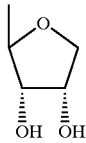

d

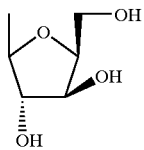

e

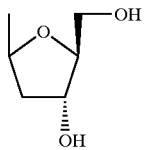

f

Further examples of the compounds of formula (I) above include Examples 1 to 65 as described hereinafter.

As used herein the term alkyl as a group or part of a group means a straight or branched chain alkyl group. Such alkyl groups preferably have 1–6 carbon atoms, most preferably 1 to 4 and in particular include methyl, ethyl, i-propyl, t-butyl. References to alkenyl groups include groups which may be in the E- or Z- form or a mixture thereof and which when they contain at least three carbon atoms, may be branched. The term halo includes chloro, bromo, fluoro and iodo. The term haloC$_{1-6}$ alkyl means an alkyl group in which one or more hydrogens is replaced by halo and preferably containing one, two or three halo groups. Examples of such groups include trifluoromethyl and fluoroisopropyl.

The term aryl as a group or part of a group means phenyl optionally substituted with one or more substituents selected from C$_{1-6}$ alkoxy (for example, methoxy), nitro, a halo atom (for example chloro), amino, carboxylate and hydroxy. The term heterocyclyl as a group or part of a group means a saturated or partially saturated (i.e. non-aromatic) 3-,4-,5- or 6 membered ring containing one or more (for example one to four) heteroatoms independently selected from nitrogen, oxygen and sulphur. Examples of such groups include pyrrolidine. The term heteroaryl means a 4,5 or 6-membered aromatic ring containing one or more (for example one to four) heteroatoms independently selected from nitrogen, oxygen and sulphur, for example: pyrazole, pyrrole, imidazole, and pyridine.

The present invention includes within its scope each possible alpha and beta anomer of the compounds of formula (I) and their physiologically functional derivatives, substantially free of the other anomer, that is to say no more than about 5% w/w of the other anomer, preferably no more than about 2% w/w, in particular less than 1% w/w will be present, and mixtures of such alpha and beta anomers in any proportions. Compounds of formula (I) in the beta anomeric form are preferred.

Preferred compounds of formula (I) include those wherein:

(i) R$^1$ is —NR$^8$R$^9$, where R$^8$ and R$^9$, which may be the same or different, are selected from C$_{1-6}$alkyl or C$_{3-7}$ cycloalkyl, preferably isopropyl or cyclopropyl;

(ii) R$^2$ is hydrogen or a halo atom;

(iii) R$^3$ and R$^4$ are both a halo atom, preferably chloro;

(iv) the sugar moiety is 3'-deoxy-L-ribofuranosyl (formula (b) as hereinbefore defined);

(v) the sugar moiety is 5'-deoxy-L-ribofuranosyl (formula (c) as hereinbefore defined);

(vi) the sugar moiety is 2'-deoxy-L-ribofuranosyl (formula (f) as hereinbefore defined);

or a pharmaceutically acceptable derivative thereof.

Particularly preferred compounds of formula (I) include those wherein $R^1$ is —$NR^8R^9$ wherein $R^8$ is hydrogen and $R^9$ is a $C_{1-6}$ alkyl, preferably isopropyl or $C_{3-7}$ cycloalkyl, preferably cyclopropyl;

$R^2$ is hydrogen or a halo atom (for example bromo), $R^3$ and $R^4$ are both a halo atom, preferably chloro and the sugar moeity is selected from:
3'-deoxy-L-ribofuranosyl;
5'-deoxy-L-ribofuranosyl; and
2'-deoxy-L-ribofuranosyl;

or a pharmaceutically acceptable derivative thereof.

Preferred compounds according to the invention include:
4-Bromo-5,6-dichloro-2-isopropylamino-1-(beta-L-ribofuranosyl)1H-benzimidazole;
5,6-Dichloro-1-(3-deoxy-beta-L-ribofuranosyl)-2-isopropylamino-1H-benzimidazole;
5,6-Dichloro-1-(5-deoxy-beta-L-ribofuranosyl)-2-isopropylamino-1H-benzimidazole;
5,6-Dichloro-1-(beta-L-erythrofuranosyl)-2-isopropylamino-1H-benzimidazole;
5,6-Dichloro-2-isopropylamino-1-(beta-L-xylofuranosyl)-1H-benzimidazole;
1-(2-Deoxy-beta-L-ribofuranosyl)-5,6-dichloro-2-isopropylamino-1H-benzimidazole;
2-Isopropylamino-1-beta-L-ribofuranosyl)-4,5,6-trichloro-1H-benzimidazole;
4-Bromo-2-cyclopropylamino-5,6-dichloro-1-(beta-L-ribofuranosyl)-1H-benzimidazole;
2-Cyclopropylamino-1-(beta-L-ribofuranosyl)-4,5,6-trichloro-1H-benzimidazole;
4,6-Dichloro-2-isopropylamino-1-(beta-L-ribofuranosyl)-1H-benzimidazole;
1-(beta-L-Erythrofuranosyl)-2-isopropylamino-4,5,6-trichloro-1H-benzimidazole;
and pharmaceutically acceptable derivatives thereof.

The compounds of formula (I) above and their pharmaceutically acceptable derivatives are hereinafter referred to as the compounds according to the invention.

By "a pharmaceutically acceptable derivative" is meant any pharmaceutically or pharmacologically acceptable salt, ester or salt of such ester of a compound according to the invention, or any compound which, upon administration to the recipient, is capable of providing (directly or indirectly) a compound according to the invention, or an antivirally active metabolite or residue thereof.

Preferred esters of the compounds according to the invention are independently selected from the following groups: (1) carboxylic acid esters obtained by esterification of the 2'-, 3'- and/or 5'-hydroxy groups, in which the noncarbonyl moiety of the carboxylic acid portion of the ester grouping is selected from straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy or amino); (2) sulphonate esters, such as alkyl- or aralkylsulphonyl (for example, methanesulphonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present advantageously contains from 1 to 18 carbon atoms, particularly form 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group.

Preferred carboxylic acid esters according to the present invention include the acetate, butyrate and valerate esters, L-valyl is a particularly preferred amino acid ester.

Any reference to any of the above compounds also includes a reference to a pharmaceutically acceptable salts thereof.

Pharmaceutically acceptable salts include salts of organic carboxylic acids such as ascorbic, acetic, citric, lactic, tartaric, malic, maleic, isethionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds of formula (I) will be pharmaceutically acceptable. However, salts of acids and bases which are non-pharmaceutically acceptable may also find use, for example, in the preparation or purification of a pharmaceutically acceptable compound. All salts, whether or not derived from a pharmaceutically acceptable acid or base, are within the scope of the present invention.

Preferred salts include salts formed from hydrochloric, sulphuric, acetic, succinic, citric and ascorbic acids.

In a further aspect of the invention there are provided the compounds according to the invention for use in medical therapy. The compounds of the present invention are particularly suited to the treatment or prophylaxis of CMV infections and associated conditions. Examples of CMV conditions which may be treated in accordance with the invention have been discussed in the introduction hereinbefore.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is a herpes virus infection, such as CMV, HSV-1, HSV-2, VZV, EBV, HHV6 or HHV7. A further aspect of the invention includes a method for the treatment or prevention of the symptoms or effects of an HBV infection.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions.

In addition to the use of compounds of formula (I) in the treatment or prophylaxis of the above viral infections and associated conditions, the compounds may also be used for the treatment or prophylaxis of heart and blood vessel diseases, in particular restenosis and specifically restenosis following angioplasty.

The above compounds according to the invention and their pharmaceutically acceptable derivatives may be employed in combination with other therapeutic agents for the treatment of the above infections or conditions. Combination therapies according to the present invention comprise the administration of at least one compound of the formula (I) or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as acyclic nucleosides (e.g. acyclovir, valaciclovir, famciclovir, ganciclovir, penciclovir), and acyclic nucleoside phosphonates (e.g. (S)-1-(3-hydroxy-2-phosphonyl-methoxypropyl) cytosine (HPMC).

The present invention further includes the use of a compound according to the invention in the manufacture of a medicament for simultaneous or sequential administration with at least one other therapeutic agent, such as those defined hereinbefore.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous, intradermal and intravitreal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. (Unless otherwise indicated, all weights of active ingredient are calculated as the parent compound of formula (I); for salts or esters thereof, the weights would be increased proportionally.) The desired dose may be presented as one, two, three, four, five, six or more sub-doses administered at appropriate intervals throughout the day. In some cases the desired dose may be given on alternative days. These subdoses may be administered in unit dosage forms, for example, containing 10 to 1000 mg or 50 to 500 mg, preferably 20 to 500 mg, and most preferably 100 to 400 mg of active ingredient per unit dosage form.

Ideally, the active ingredient should be administered to achieve peak plasma concentrations of the active compound from about 0.025 to about 100 $\mu$M, preferably about 0.1 to 70 $\mu$M, most preferably about 0.25 to 50 $\mu$M. This may be achieved, for example, by the intravenous injection of a 0.1 to 5% solution of the active ingredient, optionally in saline, or orally administered as a bolus containing about 0.1 to about 250 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal buccal and sublingual), vaginal or parenteral (including subcutaneous, intramuscular, intravenous, intradermal and intravitreal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

The present invention further includes a pharmaceutical formulation as hereinbefore defined wherein a compound of formula (I) or a pharmaceutically acceptable derivative thereof and at least one further therapeutic agent are presented separately from one another and as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3 (6), 318 (1986).

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

According to a further aspect of the invention, there is provided a process for the preparation of compounds of formula (I) above and derivatives thereof which comprises:
(A) Reacting a Compound of Formula (II)

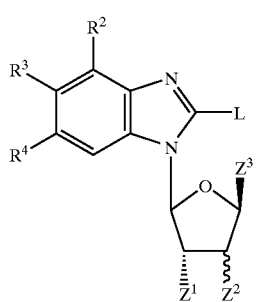

(II)

(wherein L is hydrogen, or leaving atom or group and $R^2$, $R^3$ and $R^4$ are as hereinbefore defined, $Z^1$ and $Z^2$ are the same or different and are groups $R^5$ and $R^6$ as defined in relation to formula (I) or protected hydroxy groups and $Z^3$ is a group $R^7$ as defined in formula (I) or a protected hydroxy or hydroxymethyl group) with a suitable halogenating agent such as N-bromosuccinamide or when L is a suitable leaving atom or group, for example, a halo atom such as bromine or an organo (for example alkyl) sulphone, or organo (for example alkyl or aralkyl) sulphate such as methylsulphone $(MeS(O)_2)$, methylsulphonate $(MeS(O)_2O)$ or tosylate $(4\text{-MePhS}(O)_2O)$ group and $R^2$, $R^3$ and $R^4$, $Z_1$, $Z^2$ and $Z^3$ are as hereinbefore defined, with an amine of formula H—$NR^8R^9$ (wherein $R^8$ and $R^9$ are as hereinbefore defined), a hydrazine of formula H—$NHNR^{11}R^{12}$ (wherein $R^{11}$ and $R^{12}$ are as hereinbefore defined), an alkylazo of formula H—$NNC_{1-6}$ alkyl, an alkoxyamino of formula H—N=$HOC_{1-6}$ alkyl,
or a suitable displacing agent, such as tetrabutyl ammonium azide or sodium or potassium azide;
(B) Reacting a Compound of Formula (III)

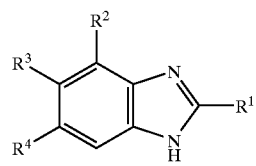

(III)

(wherein $R^1$, $R^2$, $R^3$ and $R^4$ are as hereinbefore defined) with a compound of formula (IV)

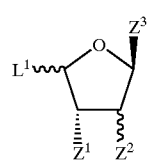

(IV)

(wherein $Z^1$ $Z^2$ and $Z^3$ as hereinbefore defined and $L^1$ is a suitable leaving group or atom in the alpha or beta position, for example, a halo (for example fluoro, chloro or bromo), an alkyl- or aryl-thio (for example phenylthio), or an aryl or aliphatic ester group such as benzoate or acetate;
and thereafter or simultaneously therewith one or more of the following further steps may be additionally performed in any desired or necessary order:
(i) removing any remaining protecting group(s);
(ii) converting a compound of formula (I) or a protected form thereof into a further compound of formula (I) or a protected form thereof;
(iii) converting the compound of formula (I) or a protected form thereof into a pharmaceutically acceptable derivative of the compound of formula (I) or a protected form thereof;
(iv) converting a pharmaceutically acceptable derivative of the compound of formula (I) or a protected form thereof into the compound of formula (I) or a protected form thereof;
(v) converting a pharmaceutically acceptable derivative of the compound of formula (I) or a protected form thereof into another pharmaceutically acceptable derivative of the compound of formula (I) or a protected form thereof;
(vi) where necessary, separating the alpha and beta anomers of the compound of formula (I) or of a protected derivative thereof or of a pharmaceutically acceptable derivative of a compound of formula (I)

Process A may conveniently be used for the preparation of a compound of formula (I) wherein $R^1$ is halogen. Such compounds may conveniently be prepared by reacting a compound of formula (II) wherein L is hydrogen and $R^2$, $R^3$, $R^4$, $Z^1$, $Z^2$ $Z^3$ are as hereinbefore defined with a halogenating agent. Halogenation may be effected in a conventional manner, for example, bromination using a brominating agent such as N-bromosuccinimide (NBS) in an aprotic solvent such as tetrahydrofuran (THF) or preferably 1,4 dioxane heated to 60–150° C., preferably 100° C.

Compounds of formula (I) wherein $R^1$ is —$NR^8R^9$ or —$NHNR^{11}R^{12}$ (wherein $R^8$, $R^9$, $R^{10}$ and $R^{11}$ are as hereinbefore defined), —N═$NC_{1-6}$ alkyl, or —$NHOC_{1-6}$ alkyl may conveniently be prepared from compounds of formula (II) wherein L is a halo atom, such as a bromo or chloro atom, by reaction with an appropriate amine $HNR^8R^9$, a hydrazine $HNHNR^{11}R^{12}$ (wherein $R^8$, $R^9$, $R^{10}$ and $R^{11}$ are as hereinbefore defined), an azoalkyl HN═$NC_{1-6}$ alkyl or alkoxyamine $HNHOC_{1-6}$ alkyl. Typically, the reaction is effected at an elevated temperature, for example, 70–80° C. in an organic solvent such as ethanol or dimethylsulfoxide.

Compounds of formula (I) wherein $R^1$ is azido may advantageously be prepared from compounds formula (II), wherein L is a halo atom, such as bromo or chloro, by reaction with a suitable displacing agent such as sodium or potassium azide or tetrabutyl ammonium azide in an aprotic solvent such as THF or 1,4 dioxane, at an elevated temperature such as 60–150° C., more particularly 100° C.

Compounds of formula (II) wherein $Z^1$ and/or $Z^2$ are hydroxy groups and/or $Z^3$ is a hydroxy or hydroxymethyl group can, for example, be prepared from a corresponding compound of formula (II) wherein $Z^1$ and/or $Z^2$ are each a protected hydroxy group and/or $Z^3$ is a protected hydroxy or hydroxymethyl group. Conventional protecting groups may be used for $Z^1$, $Z^2$ and $Z^3$. Advantageously ester groups such as those described above in relation, to the esters of the compounds of formula (I) may be used. These protecting groups may be removed either by conventional chemical techniques such as sodium carbonate in methanol or enzymatically, for example, using pig liver enzyme. Alternatively, $Z^1$, $Z^2$ and $Z^3$ may include silyl protecting groups such as tert-butyldiphenyl-, tert-butyldimethyl-, triisopropropyl-silyl groups which may be removed using an appropriate fluoride source, for example HF/Pyridine, n-$Bu_4NF$ or $Et_4NF$ or a cyclic acetal or ketal such as benzylidene or isopropylidene groups which can be removed under acidic conditions, for example, using tosic acid and methanol.

Alternatively, the compound of formula (II) where $Z^1$ and/or $Z^2$ are protected hydroxy groups and/or $Z^3$ is a protected hydroxy or hydroxymethyl group may be reacted with an agent or under conditions whereby the leaving group L is converted to the desired $R^1$ group simultaneously with removal of the protecting groups. Examples of such agents include cyclopropylamine and other primary and secondary amines providing that these agents are sufficiently nucleophilic and are not sterically hindered.

Compounds of formula (II) wherein L, $R^2$, $R^3$ and $R^4$ are as hereinbefore defined, $Z^1$ is a protected hydroxy group, $Z^2$ is hydrogen and $Z^3$ is a protected hydroxymethyl group may be synthesised from a corresponding compound of formula (II) wherein L, $R^2$, $R^3$ and $R^4$ are as hereinbefore defined, $Z^1$ is a hydroxy group, $Z^2$ is an erythro hydroxy group and $Z^3$ is a hydroxymethyl group according to the procedure of Kawana et al. J. Chem. Soc., Perlan Trans. I, 1989, 1593–1596.

Compounds of formula (II) wherein L, $R^2$, $R^3$ and $R^4$ are as hereinbefore defined, $Z^1$ is hydrogen, $Z^2$ is a protected erythro hydroxy group and $Z^3$ is a protected hydroxymethyl group may be prepared from the corresponding compound wherein C2 is hydroxy using the Bartons deoxygenation process as described in D. H. R. Barton, J.Cs. Jaszberenyi Tetrahedron Lett. 1989, 30, 2619–2622. The C2 hydroxy compound referred to above may be prepared from the corresponding ribose compound by treatment with an appropriate protecting agent or agents, for example, a silylating agent such as 1,3-dichloro-1,1,3,3-tetraisopropyldisiloxane in the presence of a solvent such as pyridine and at a temperature range of 5–70° C. and preferrably at ambient temperature.

Compounds of formula (I) wherein $R^1$ is as hereinbefore defined and compounds of formula (II) wherein L is as hereinbefore defined may be prepared by reacting a compound of formula (V)

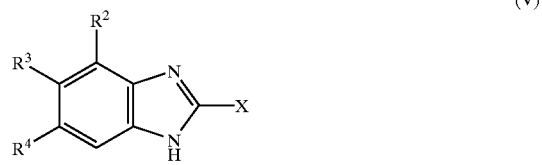

(V)

(wherein $R^2$, $R^3$ and $R^4$ are as hereinbefore defined and X is equivalent to $R^1$ or L as hereinbefore defined), with a compound of formula (IV)

(IV)

(wherein $Z^1$, $Z^2$, $Z^3$ and $L^1$ are as hereinbefore defined).

The reaction of the compounds of formula (IV) and (V) may be effected using a Lewis acid such as trimethylsilyl triflate, stannic tetrachloride, or boron trifluoride, the former being preferred. The reaction is generally effected in an aprotic solvent and at an elevated temperature, for example, in acetonitrile at 15–30° C. or 1,2-dichloroethane at 70–90° C.

The compound of formula (V) is advantageously trimethylsilylated at the $N_1$-position in the above procedures to improve solubility; for example by treatment with trimethylsilyl chloride, hexamethyl disilazane or, most preferably, N,O-bis-trimethylsilyl acetamide (BSA). This silylation can be effected in a solvent preferably 1,2-dichloroethane or acetonitrile preferably at 70–80° C. After completion of the silylation reaction, a Lewis acid may be added followed by addition of the compound of formula (IV).

Compounds of formula (IV) may be produced by conventional methods prior to coupling with the base or derived by modification of another sugar moiety which is already part of a nucleoside. For example, compounds of formula (IV) wherein $L^1$ is as hereinbefore defined, $Z^1$ is hydroxy or a protected hydroxy group, $Z^2$ is an erythro hydroxy or a protected erythro hydroxy group and $Z^3$ is hydroxymethyl or a protected hydroxymethyl group, may be prepared by methods analogous to those known for D-ribose derivatives or by methods readily available from the chemical literature, for example, by methods described in Acton et al. J. Am.

Chem. Soc, 1964, 86, 5352. A preferred compound of formula (IV) is the compound wherein $Z^1$ $Z^2$ and $L^1$ are each $OC(O)CH_3$ and $Z^3$ is —$CH_2OC(O)CH_3$. This compound may be prepared in an analogous manner to that developed for D-ribose (R. D. Guthrie and S. C. Smith., Chemistry and Industry, 1968, pp 547–548), followed advantageously by recrystallisation from ethanol.

Compounds of formula (IV) wherein $L^1$ is as hereinbefore defined, $Z^1$ and $Z^2$ are protected erythro hydroxy groups and $Z^3$ is $CH_3$ or $CH_2R^{13}$ wherein $R^{13}$ is a halo atom including Cl, Br, F and I, may be synthesised from the corresponding sugar moiety wherein C1 is an appropriate ether group such as an aryloxy, arylalkyloxy (e.g. benzyloxy) or alkoxy (e.g. methoxy) by treatment with an appropriate esterifying agent, such as an acylating agent, for example, an acid anhydride, such as acetic anhyridie or benzoic anhydride in the presence of a mineral acid, for example, sulphuric acid. The reaction may be done at a temperature of −20 to 30° C. and preferably at a temperature of 5° C. in a solvent such as acetic acid.

Such ethylated compounds may be synthesised from the corresponding C2, C3 diol by treatment with an appropriate esterifying agent such as an acylating agent, for example, an acid anhydride such as acetic or benzoic anhydride in an appropriate solvent such as pyridine or in an organic solvent such as acetonitrile in the presence of a base, for example, triethylamine (TEA) and a nucleophilic catalyst such as $N_1$N-dimethylaminopyridine (DMAP). Such diol compounds may conveniently be prepared by cleavage of the corresponding C2, C3 cyclic ether compound by treatment with a weak acid such as Dowex 50 in the presence of an alcohol, for example, methanol. Appropriate cyclic ethers include cyclic ketals, for example, isopropylidine.

Cyclic ether compounds wherein $Z^3$ is $CH_3$ may be prepared by dehalogenation of the corresponding compound wherein $Z^3$ is a $CH_2$halo group, for example, $CH_2Cl$ or $CH_2F$. Typically the reaction is carried out in the presence of a free radical initiater, such as -azo-iso-butyronitrile (AIBN), a solvent, for example, toluene and at a temperature in the range of 70 to 110° C. for example 90° C. Compounds wherein $Z^3$ is a $CH_2$halo group may be prepared by halogenation of the corresponding sugar moiety wherein $Z^3$ is $CH_2OH$. Halogenation may be effected in a conventional manner, for example, chlorination using an agent such as triphenyl phosphine ($Ph_3P$) in an organic solvent, for example, acetonitrile.

Such halomethyl compounds may be prepared from commercially available L-ribose by treatment with an alcohol, for example, methanol in a mineral acid, for example, sulphuric acid in a temperature range of 0–50° C., conveniently at room temperature, followed by treatment with an protecting agent, such as 2,2-dimethoxypropane in an appropriate aprotic solvent such as tetrahydrofuran or preferably 2,2-dimethoxypropane itself. The reaction may be carried out in a temperature range of minus 10 to 60° C. and preferably at ambient temperature.

Compounds of formula (IV) wherein $L^1$ is as hereinbefore defined, $Z^1$ is an erythro protected hydroxy group, $Z^2$ is a threo protected hydroxy group and $Z^3$ is a protected hydroxymethyl group may be synthesised from L-xylose in a manner analogous to that described by Gosselin et al (Nucleic Acid Chemistry Improved and New Synthetic Procedures, Methods and Techniques, Part 4. Ed. L B Townsend, R S Tipson) starting from D-xylose.

Compounds of formula (IV) wherein $L^1$ is as hereinbefore defined, $Z^1$ and $Z^2$ are protected erythro hydroxy groups and $Z^3$ is hydrogen may conveniently be prepared by treating the corresponding sugar moiety wherein $C^1$ is hydroxy and $C_2$ and $C_3$ are ether groups, for example, cyclic ketals such as isopropylidine. Such vicinal sugar moieties may be prepared by the method described by Hudlicky et al 1990, J. Org. Chem., 55, 4683.

Compounds of formula (V) wherein X is L or a —$NR^8R^9$ group (wherein L, $R^8$ and $R^9$ are as hereinbefore defined), may be prepared in accordance with the methods described in PCT specification WO92/07867 incorporated herein by reference.

Alternatively, compounds of formula (V) wherein X is R and R is a group —$NR^8R^9$ wherein $R^8$ and $R^9$ are as hereinbefore defined may be prepared by reacting a compound of formula (VI).

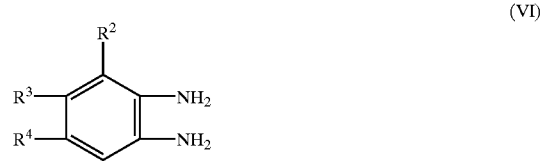

with an agent or agents capable of cyclising the diamine into a benzimidazole. Typically compounds of formula (I) may be reacted with an isothiocyanate of formula (VII)

wherein $R^8$ and $R^9$ are as hereinbefore defined.

The reaction may be carried out in the presence of a carbodiimide such as dicyclohexyl carbodiimide or 1-cylohexyl-3-(2-morpholinoethyl)carbodiimide metho-p-toluene-sulphonate conveniently in the presence of an aprotic aromatic solvent such as toluene and most preferably pyridine and at an elevated temperature, preferably 75–150° C.

Compounds of formula (V) wherein X is hydrogen may be obtained commercially or alternatively may be prepared by reacting a compound of formula (VI) with formamidine under aqueous acidic conditions, at room temperature to 80° C.

Compounds of formula (VI) may be prepared from the appropriate corresponding othro nitro aniline in the presence of a reducing agent such as reduced iron, for example, in the presence of an acid, most preferably hydrochloric acid. This reaction is typically carried out in the presence of a solvent, ethyl alcohol for example, in a temperature range of 50–78° C. (B. Fox and T. L. Threfall, Org. Syn. Coll. Vol. 5, 1973, p. 346). Alternatively, such ortho phenylenediamines may be prepared in the presence of a reducing agent such as catalytic Raney nickel, also in the presence of hydrogen. This reaction is typically run in the presence of a solvent, ethyl alcohol for example, at ambient temperatures (K. Dimroth, et al, Org. Syn. Coll. Vol. 5, 1973, p. 1130). More particularly, such ortho phenylenediamines may be prepared by methods described in the literature.

Compounds of formula (VI) and (VII) may be prepared by methods well known to a skilled person or readily available in the chemical literature or obtained commercially.

Esters according to the invention may be prepared by methods well known in the art, for example, a compound of formula (I) may be converted into a pharmaceutically acceptable ester by reaction with an appropriate esterifying agent, for example, an appropriate acid halide or anhydride.

A compound of formula (I) may be converted into a corresponding pharmaceutically acceptable ether of formula (I) by reaction with an appropriate alkylating agent in a conventional manner.

The compounds of formula (I) including esters thereof, may be converted into pharmaceutically acceptable salts thereof in conventional manner, for example by treatment with the appropriate acid. An ester or salt of an ester of formula (I) may be converted into the parent compound, for example, by hydrolysis.

The beta and alpha anomers may be separated and isolated in pure form by silica gel chromatography using a single solvent or a combination of solvents such as 1:20 methanol:dichloromethane.

The following Examples are intended for illustration only and are not intended to limit the scope of the invention in any way. The term 'active ingredient' as used in the Pharmaceutical examples means a compound of formula (I) or a pharmaceutically acceptable derivative thereof. The term also covers a compound of formula (I) or a pharmaceutically acceptable derivative thereof in combination with one or more therapeutic agents.

EXAMPLE 1

Tablet Formulations

The following formulations A and B were prepared by wet granulation of the ingredients with a solution of povidone, followed by addition of magnesium stearate and compression.

| Formulation A | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |

| Formulation B | mg/tablet | mg/tablet |
|---|---|---|
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |

| Formulation C | mg/tablet |
|---|---|
| Active ingredient | 100 |
| Lactose | 200 |
| Starch | 50 |
| Povidone | 5 |
| Magnesium stearate | 359 |

The following formulations, D and E, were prepared by direct compression of the admixed ingredients. The loctose used in formulation E was of the direct compression type (Dairy Crest—"Zeparox").

| Formulation D | mg/tablet |
|---|---|
| Active Ingredient | 250 |
| Pregelatinised Starch NF15 | 150 |
| | 400 |

| Formulation E | mg/tablet |
|---|---|
| Active Ingredient | 250 |
| Lactose | 150 |
| Avicel | 100 |
| | 500 |

Formulation F (Controlled Release Formulation)

The formulation was prepared by wet granulation of the ingredients (below) with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

EXAMPLE 2

Capsule Formulations

Formulation A

A capsule formulation was prepared by admixing the ingredients of Formulation D in Example 1 above and filling into a two-part hard gelatin capsule. Formulation B (infra) was prepared in a similar manner.

| Formulation B | mg/tablet |
|---|---|
| (a) Active ingredient | 250 |
| (b) Lactose B.P. | 143 |
| (c) Sodium Starch Glycollate | 25 |
| (d) Magnesium Stearate | 2 |
| | 420 |

| Formulation C | mg/tablet |
|---|---|
| (a) Active ingredient | 250 |
| (b) Macrogol 4000 BP | 350 |
| | 600 |

Capsules were prepared by melting the macrogol 4000 BP, dispersing the active ingredient in the melt and filling the melt into a two-part hard gelatin capsule.

| Formulation D | mg/tablet |
|---|---|
| Active ingredient | 250 |
| Lecithin | 100 |
| Arachis Oil | 100 |
| | 450 |

Capsules were prepared by dispersing the active ingredient in the lecithin and arachis oil and filling the dispersion into soft, elastic gelatin capsules.

Formulation E (Controlled Release Capsule)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

| | mg/tablet |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE 3

Injectable Formulation

| Formulation A | |
|---|---|
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient was dissolved in most of the water (35°–40° C. and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealed with sterile closures and overseals.

| Formulation B | |
|---|---|
| Active ingredient | 0.125 g |
| Sterile, pyrogen-free, pH7 phosphate buffer, | q.s. to 25 ml |

EXAMPLE 4

| Intramuscular injection | |
|---|---|
| Active ingredient | 0.20 g |
| Benzyl Alcohol | 0.10 g |

-continued

| Intramuscular injection | |
|---|---|
| Glycofurol | 1.45 g |
| Water for Injection | q.s. to 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE 5

| Syrup | |
|---|---|
| Active ingredient | 0.2500 g |
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water | q.s. to 5.0000 ml |

The active ingredient was dissolved in a mixture of the glycerol and most of the purified water. An aqueous solution of the sodium benzoate was then added to the solution, followed by addition of the sorbitol solution and finally the flavour. The volume was made up with purified water and mixed well.

EXAMPLE 6

| Suppository | mg/suppository |
|---|---|
| Active Ingredient (631 m)* | 250 |
| Hard Fat, BP (Witepsol H15-Dynamit Nobel) | 1770 |
| | 2020 |

*The active ingredient was used as a powder wherein at least 90% of the particles were of 631 m diameter or less.

One-fifth of the Witepsol H15 was melted in a steam-jacketed pan at 45° C. maximum. The active ingredient was sifted through a 1001 m sieve and added to the molten base with mixing, using a silverson fitted with a cutting head, until a smooth dispersion was achieved. Maintaining the mixture at 45° C., the remaining Witepsol H15 was added to the suspension and stirred to ensure a homogeneous mix. The entire suspension was passed through a 2501 m stainless steel screen and, with continuous stirring, was allowed to cool to 40° C. At a temperature of 38° C. to 40° C., 2.02 g of the mixture was filled into suitable, 2 ml plastic moulds. The suppositories were allowed to cool to room temperature.

CHEMICAL EXAMPLES

EXAMPLE 1

2-Cyclopropylamino-5,6-dichloro-1-(5-deoxy-beta-L-ribofuranosyl)-1H-benzimidazole Cyclopropylamine (5 mL) and 2-bromo-5,6-dichloro-1-(5-deoxy-2,3-diacetyl-beta-L-ribofuranosyl)-1H- benzimidazole (0.45 g, 0.96 mmol) were combined with absolute ethanol (15 mL) and stirred at 80° C. for 24 h. The reaction mixture was concentrated and purified on a silica gel column (2.5×18 cm, 230–400 mesh) with 1:5 methanol:dichloromethane to give 0.42 g of crude product. This material was further purified on a second silica gel column (2.5×18 cm, 230–400 mesh) with 1:2 hexanes ethyl:acetate to give a white solid (0.050 g, 0.14 mmol, 31%); m.p. 186–187° C.; $[\alpha]^{20}{}_D$=(+) 62.0 (c=0.5 DMP); UV $\lambda_{max}$ ($\epsilon$): pH 7.0:302 nm (9,500), 275 (1,800), 259 (9,100); MS (CI) m/z (rel. intensity) 357 (3.16, M-1); $^1$H NMR (DMSO-$d_6$) d 7.46 (s, 1H, Ar—H), 7.33 (s, 1H, Ar—H), 7.10 (d, 1H, NH, J=2.4 Hz), 5.59 (d, 1H, H-1', J=6.6 Hz), 5.22 (d, 1H, OH, J=4.8 Hz), 5.20 (d, 1H, OH, J=7.2 Hz), 4.30 (q, 1H, H-4', J=6.6 Hz), 3.89 (m, 1H), 3.79–3.75 (m, 1H), 2.77–2.71 (m, 1H, cyclopropyl-CH), 1.34 (d, 6H, H-5', J=6.6 Hz), 0.70–0.67 (m, 2H, cyclopropyl-CH$_2$), 0.56–0.48 (m, 2H, cyclopropyl-CH$_2$).

Anal. Calcd. for $C_{15}H_{17}N_3O_3Cl_2$: C, 50.29; H, 4.78; N, 11.73. Found: C, 50.38; H, 4.88; N, 11.52.

EXAMPLE 2

2-Cyclopentylamino-5,6-dichloro-1-(5-deoxy-beta-L-ribofuronosyl)-1H-benzimidazole Cyclopentylamine (1 mL) and 2-bromo-5,6-dichloro-1-(5-deoxy-2,3-diacetyl-beta-L-ribofuranosyl)-1H-benzimidazole (0.40 g 0.86 mmol) were combined with absolute ethanol (10 mL) and stirred at 80° C. for 24 h. The reaction mixture was concentrated and purified on a silica gel column (2.5×18 cm, 230–400 mesh) with 1:20 methanol:dichloromethane to give 0.36 g of crude product. This material was further purified on a second silica gel column (2.5×17 cm, 230–400 mesh) with 1:1 hexanes ethyl:acetate to give a white solid (0.27 g, 0.70 mmol, 81%); m.p. 172–173° C.; $[\alpha]^{20}{}_D$=(+) 39.6 (c=0.5 DMF); UV $\lambda_{max}$ ($\epsilon$): pH 7.0:304 nm (10,200), 276 (2,000), 260 (9,400); MS (CI): m/z (rel. intensity) 386 (65.63, M$^-$); $^1$H NMR (DMSO-$d_6$) d 7.40 (s, 1H, Ar—H), 7.31 (s, 1H, Ar—H), 6.62 (d, 1H, NH, J=6.8 Hz), 5.70 (d, 1H, H-1', J=6.9 Hz), 5.23 (d, 1H, OH, J=3.6 Hz), 5.21 (d, 1H, OH, J=6.9 Hz), 4.30 (q, 1H, H-4', J=6.7 Hz), 4.19–4.12 (m, 1H, cyclopentyl-CH), 3.95–3.87 (m, 1H), 3.81–3.76 (m, 1H), 2.49–2.47 (m, 2H, cyclopentyl-CH$_2$), 1.97–1.93 (m, 2H, cyclopentyl-CH$_2$), 1.36 (d, 3H, H-5', J=6.3 Hz).

Anal. Calcd. for $C_{17}H_{21}N_3O_3Cl_2$: C, 52.86; H, 5.48; N, 10.88. Found: C, 52.93; H, 5.50; N, 10.77.

EXAMPLE 3

2-Isopropylamino-5,6-dichloro-1-(5-deoxy-beta-L-ribofuranosyl)-1H-benzimidazole

Isopropylamine (5 mL ) and 2-bromo-5,6-dichloro-1-(5-deoxy-2,3-diacetyl-beta-L-ribofuranosyl)-1H-benzimidazole (0.40 g, 0.86 mmol) were combined with absolute ethanol (20 mL) and stirred at 80° C. for 24 h. The reaction mixture was concentrated and purified by multiple cyclings on a chromatotron fitted with a 2 mm silica gel rotor, with 1:30 methanol:dichloromethane and 1:1 ethyl acetate:hexanes and 1:4 acetone:dichloromethane to give a white solid (0.18 g, 0.70 mmol, 60%); m.p. 103–105° C.; $[\alpha]^{20}{}_D$=(+) 38.8 (c=0.5 DMF); UV $\lambda_{max}$ ($\epsilon$): pH 7.0:303 nm (10,400), 276 (2,500), 260 (10,000); MS (CI): m/z (rel. intensity) 360 (14.26, M$^-$); $^1$H NMR (DMSO-$d_6$) d 7.39 (s, 1H, Ar—H), 7.31 (s, 1H, Ar—H), 6.57 (d, 1H, NH, J=7.6 Hz), 5.68 (d, 1H, H-1', J=6.6 Hz), 5.23 (d, 1H, OH, J=4.8 Hz), 5.21 (d, 1H, OH, J=7.1 Hz), 4.31 (q, 1H, H-4', J=6.7 Hz), 4.04–3.98 (m, 1H, isopropyl-CH), 3.95–3.87 (m, 1H), 3.81–3.76 (m, 1H), 1.36 (d, 3H, H-5', J=6.5 Hz), 1.20 (d, 6H, cyclopentyl-CH$_2$, J=6.6 Hz).

Anal. Calcd. for $C_{15}H_{19}N_3O_3Cl_2$: C, 50.01; H, 5.32; N, 11.66. Found: C, 49.88; H, 5.38; N, 11.36.

EXAMPLE 4

2-Bromo-5,6-dichloro-1-(5-deoxy-beta-L-ribofuranosyl)-1H-benzimidazole

A solution of 2-bromo-5,6-dichloro-1-(2,3-di-O-acetyl-5-deoxy-beta-L-ribofuranosyl)-1H-benzimidazole(0.95 g, 2.0 mmol) in methanol (17 mL) and ethanol (17 mL) was combined with a solution of sodium carbonate (0.22 g, 2.1 mmol) in water (4 mL). The solution was stirred at rt for 2 h, then acetic acid (0.24 mL, 4 mmol) was added and the methanol and ethanol were removed on the rotoevaporator. The solution was then extracted between ethyl acetate (150 ml) and water (2×50 mL). The organics were concentrated and purified on a silica gel column (25×17 cm, 230–400 mesh) with 1:20 methanol:dichloromethane. Further purification on a chromatotron fitted with a 2 mm rotor using 1:8 acetone:dichloromethane provided a white solid (0.43 g, 1.1 mmol, 57%); m.p. 136–138° C.; $[\alpha]^{20}{}_D$=(+) 71.0 (c=0.5 DMF); UV $\lambda_{max}$ ($\epsilon$): pH 7.0:299 nm (8,300), 273 (3,200), 255 (8,500), 241 (5,100); MS (CI): m/z (rel. intensity) 382 (2.24, M$^+$); $^1$H NMR (DMSO-$d_6$) d 7.97(s, 1H, Ar—H), 7.85 (s, 1H, Ar—H), 5.84 (d, 1H, H-1', J=6.8 Hz), 5.49 (d, 1H, OH, J=6.0 Hz), 5.26 (d, 1H, OH, J=5.0 Hz), 4.48 (q, 1H, H-4', J=6.4 Hz), 4.02–3.97 (m, 1H), 3.95–3.85 (m, 1H), 1.40 (d, 3H, H-5', J=6.5 Hz).

Anal. Calcd. for $C_{12}H_{11}N_2O_3Cl_2Br$: C, 37.73; H, 2.90; N, 7.33. Found: C, 37.84; H, 2.99; N, 7.32.

EXAMPLE 5

2-Bromo-5,6-dichloro-1-(2,3-di-O-acetyl-5-deoxy-beta-L-ribofuranosyl)-1H-benzimidazole 2-Bromo-5,6-dichlorobenzimidazole (1.9 g, 7.0 mmol), N,O-bis(trimethylsiyl) acetamide (2.1 mL, 10.5 mmol), and acetonitrile (50 mL) were combined and refluxed under nitrogen for 20 min. The solution was cooled to rt and trimethylsilyl triflate (2.5 ml, 12.8 mmol) was added. After 15 min a solution of 1,2,3-tri-O-acetyl-5-deoxyribofuranose in acetonitrile (10 mL) was added. The solution was stir under nitrogen at rt for 2 h, then diluted with 1:2 hexanes:ethyl acetate (150 mL) and extracted with cold 10% aqueous sodium bicarbonate (50 mL) and water (50 mL). The organic layers were dried with magnesium sulfate (anhyd), filtered, and evaporated. The crude residue was purified on a silica gel column (5×16 cm, 230–400 mesh) with neat dichloromethane then with (1:50) acetone:dichloromethane to give 2-bromo-5-dichloro-1-(2,3-tri-O-acetyl-beta-ribofuranosyl)-1H-benzimidazole (2.3 g, 5 mmol, 71%); m.p. 68–70° C.; $[\alpha]^{20}{}_D$=(+) 26.4 (c=0.5 DMF); MS (CI): m/z 489 (M$^+$+Na$^+$, 1.52) $^1$H NMR (DMSO-$d_6$) $\delta$ 8.09 (s, 1H, Ar—H), 7.97 (s, 1H, Ar—H), 6.12 (d, 1H, J=6.9 Hz), 5.63 (t, 1H, H-2', J=6.9 Hz), 5.25 (t, 1H, H-3', J=6.5 Hz), 4.27–4.19 (m, 1H, H-4'), 2.11 (s, 3H, OAc), 2.00 (s, 3H, OAc), 1.48 (d, 3H, H-5', J=6.6 Hz).

Anal. Calcd. for $C_{16}H_{15}N_2O_5Cl_2Br$: C, 41.23; H, 3.24; N, 6.01. Found: C, 41.42; H, 3.24; N, 6.08.

EXAMPLE 6

5-Deoxy-1,2,3-tri-O-acetyl-L-ribofuranose

Methyl 5-deoxy-2,3-di-O-acetyl-L-ribofuranoside (3.3 g, 15.2 mmol) was dissolved in acetic add (20 mL) and acetic anhydride (5 mL). The solution was cooled to ice bath temperature and concentrated sulfuric acid was added dropwise (1 mL). The solution was kept at 5° C. for 4 days, then it was poured into ice water (50 mL) and extracted with 3:1 ethyl acetate:hexanes (200 mL and 75 mL). The combined organics were washed with 10% sodium bicarbonate (2×50 mL) and water (50 mL). The organic layers were dried, and concentrated and the residue purified on a silica gel column (5×15 cm, 230–400 mesh) with ethyl acetate:hexanes (1:3). Both anomers were observed but were isolated together as a clear oil (2.2 g, 8.8 mmol, 58%); $^1$H NMR (DMSO-d$_6$) δ 5.96 (d, 1H, J=1 Hz), 5.23 (d, 1H, H-2, J=5 Hz), 4.96 (t, 1, H-3, J=5.7 Hz), 4.24–4.16 (m, 1H, H-4), 2.07 (s, 3H, OAc), 2.05 (s, 3H, OAc), 2.02 (s, 3H, OAc), 1.27 (d, 3H, H-5, J=6.3 Hz).

Anal. Calcd. for $C_{11}H_{16}O_7$: C, 50.77; H, 6.20. Found: C, 50.59; H, 6.17.

EXAMPLE 7

Methyl 5-deoxy-2,3-di-O-acetyl-L-ribofuranoside

Methyl 5-deoxy-L-ribofuranoside (2.25 g, 15.2 mmol) was combined with acetic anhydride (10 ml, 106 mmol), triethylamine (20 mL), and N,N-dimethylaminopyridine (0.2 g, 1.6 mmol) in acetonitrile (100 mL). The solution was stirred at rt for 18 h, then concentrated to a thick oil, then dissolved in 150 mL of ethyl acetate:hexanes (3:1) and extracted with saturated sodium carbonate (2×25 mL) and water (25 mL). The organic layer was dried and concentrated to a yellow oil (3.3 g, 14.2 mmol, 93%) which was used directly without further purification.

EXAMPLE 8

Methyl 5-deoxy-L-ribofuranoside

Methyl 5-deoxy-2,3-O-isopropylidene-L-ribofuranoside (7.1 g, 37.7 mmol) was combined with 80% trifluoroacetic acid (50 ml) and stirred at ambient temperature for four hours. The solvents were removed in vacuo. The crude product was treated with $H_2SO_4$ (0.5 mL) in methanol (50 mL) at rt for 18 hour then quenched with solid NaHCO$_3$, filtered and concentrated. The gold residue was purified on a silica gel column (5×18 cm) with 1:15 methanol:dichloromethane. Product was isolated as a mixture of the beta and alpha anomers: (2.25 g, 15.2 mmol, 40%), which was used directly without further purification. MS (API-; m/z (rel intensity) 1.47 (100, M-H); $^1$H NMR (DMSO-d$_6$) δ 4.95 (d, 1H, 2-OH, J=4.3 Hz), 4.77 (d, 1H, 3-OH, J=6.8), 4.75 (d, 1H, H-1, J=1 Hz), 3.80 (apparent pentuplet, 1H, H-4, J=6.3 Hz, J=6.8 Hz), 3.70 (apparent dt, 1H, H-2, J=4.3 Hz, J=4.7 Hz, J=1 Hz), 3.61 (apparent dt, 1H, H-3, J=6.8, J=6.8, J=4.7), 3.19 (s, 3H, OMe), 1.16 (d, 3H, H-5, J=6.3 Hz).

EXAMPLE 9

Methyl 5-deoxy-2,3-isopropylidene-beta-L-ribofuranoside

Methyl 5-chloro-5-deoxy-2,3-isopropylidene-L-ribofuranoside was combined with azobis(isobutylnitrile, AIBN) (0.33 g, 0.4 mmol) and toluene. The solution was purged with dry nitrogen for 20 minutes. Tributyltin hydride was added and the solution was warmed to 90° C. for 18 h. The reaction mixture was concentrated, redissolved in ether (100 mL) and combined with one equivalent of KF in water (50 mL). After 30 min. a white precipitate was filtered off and the two phases were separated. The organics were dried ($Na_2SO_4$), filtered and concentrated. The residue was purified on a silica gel column (5×16 cm) with 1:8 ethyl acetate:hexanes. Pure product was obtained as a clear oil: (7.3 g, 39 mmol, 94%); $[α]^{20}_D$=(−) 0.6 (c=0.5 DMF); MS (AP+): m/z (rel. intensity) 178.8 (100, M-CH$_3$); $^1$H NMR (DMSO-d$_6$) δ 4.83 (s, 1H, H-1), 4.58 (d, 1H, H-2, J=6.0 Hz), 4.52 (d, 1H, H-3, J=6.0 Hz), 4.20 (q, 1H, H-4, J=7.0 Hz), 3.21 (s, 3H, OMe), 1.35 (s, 3H, CH$_3$), 1.22 (s, 3H, CH$_3$), 1.17 (d, 3H, H-5, J=7.1 Hz).

Anal. Calcd. for $C_9H_{16}O_4 \cdot 0.5 C_6H_{14}$: C, 58.02; H, 8.74. Found: C, 58.31; H, 8.47.

EXAMPLE 10

Methyl 5-chloro-2,3-isopropylidene-beta-L-ribofuranoside

Methyl 2,3-isopropylidene-beta-L-ribofuranoside (16.5 g, 80.8 mmol) was combined with anhydrous acetonitrile and carbon tetrachloride. Triphenylphosphine was added and this solution was stirred under nitrogen at ambient temperature. After 18 h the solution was concentrated to a thick suspension. This mixture was partially purified on a silica gel filter pad (4×14 cm) with 1:2 ethyl acetate:hexanes to give a light yellow oil product: (17.8 g, 80 mmol, 99%); $[α]^{20}_D$=(+) 81.6 (c=0.5 DMF); MS (CI): m/z (rel. intensity) 191 (100, M-OCH$_3$); $^1$H NMR (DMSO-d$_6$) δ 4.95 (s, 1H, H-1), 4.71 (d, 1H, H-2, J=6.0 Hz), 4.59 (d, 1H, H-3, J=6.0 Hz), 4.16 (t, 1H, H-4, J=7.7 Hz), 3.58 (d, 2H, H-5, J=7.0 Hz), 3.25 (s, 3H, OMe), 1.37 (s, 3H, CH$_3$), 1.24 (s, 3H, CH$_3$).

Anal. Calcd. for $C_9H_{15}O_4Cl \cdot 0.4 C_4H_8O_2$: C, 49.36; H, 7.11. Found: C, 49.53; H, 6.83.

EXAMPLE 11

Methyl 2,3-isopropylidene-beta-L-ribofuranoside

L-ribose (15.5 g, 98 mmol) was combined with methanol (150 mL) and concentrated sulfuric acid (0.5 mL). This solution was stirred at ice bath temperature for 18 h. 2,2-Dimethoxypropane (300 mL) was added to the solution and stirring was continued at ambient temperature for 18 h more. Pyridine (40 mL) was added and the solution was concentrated. The residue was partitioned between ethyl acetate (300 mL) and 1N HCl (4×100 mL), and then the organics were washed with 10% NaHCO$_3$, dried with Na$_2$SO$_4$, decanted and concentrated. The residue was a gold oil 20.0 g, 98 mmol, 95%); $[α]^{20}_D$=(+) 92.0 (c=0.5 DMF); MS (CI): m/z (rel. intensity) 2.05 (58.28, M+); $^1$H NMR (DMSO-d$_6$) δ 4.85 (s, 1H, H-1), 4.80 (d, 1H, H-2, J=6.0 Hz), 4.51 (d, 1H, H-3, J=6.0 Hz), 3.98 (t, 1H, H-4, J=5.8 Hz, J=8.9 Hz), 3.37–3.26 (m, 2H, H-5), 3.19 (s, 3H, OMe), 1.36 (s, 3H, CH$_3$), 1.23 (s, 3H, CH$_3$).

Anal. Calcd. for $C_9H_{16}O_5$: C, 52.93; H, 7.90. Found: C, 52.90; H, 7.88.

EXAMPLE 12

1-(5-Chloro-5-deoxy-beta-L-ribofuranosyl)-5,6-dichloro-2-isopropylamino-1H-benzimidazole A solution of 1-(2,3-di-O-acetyl-5-chloro-5-deoxy-beta-L-ribofuranosyl)-5,6-dichloro-2-isopropylamino-1H-benzimidazole(0.52 g, 1.1 mmol) in methanol (10 mL) and ethanol (10 mL) was combined with a solution of sodium carbonate (0.17 g, 1.6 mmol) in water (5 mL). The solution was stirred at rt for 24 h, then the methanol and ethanol were removed on the rotoevaporator. The solution was diluted with ethyl acetate (150 mL) and extracted with water (2×50 mL). The organics were dried, concentrated and purified on a silica gel column (25×17 cm, 230–400 mesh) with 1:25 methanol:dichloromethane to give a white solid (0.34 g, 0.86 mmol, 79%); m.p. 95–97° C.; $[\alpha]^{20}{}_D$=(+) 13.6 (c=0.5 DMF); UV $\lambda_{max}$ ($\epsilon$): pH 7.0:303 nm (10,800), 276 (2,300), 260 (10,300), 245 (6,600); MS (API+): m/z (rel. intensity) 394 (100, M+); $^1$H NMR (DMSO-d$_6$) δ 7.52 (s, 1H, Ar—H), 7.39 (s, 1H, Ar—H), 6.62 (d, 1H, NH, J=7.3 Hz), 5.74 (d, 1H, H-1', J=7.4 Hz), 5.45 (d, 1H, OH, J=4.5 Hz), 5.45 (d, 1H, OH, J=7.3 Hz), 4.33 (q, 1H, CH, J=6.9 Hz), 4.09–3.94 (m, 5H, H-2', H-3', H-4' and H-5'), 1.20 (d, 6H, CH(CH$_3$)$_2$).

Anal. Calcd. for $C_{15}H_{18}N_3O_3Cl_3 \cdot 0.60 CH_4O$: C, 45.27; H, 4.97; N, 10.15. Found: C, 45.17; H, 4.75; N, 10.01.

EXAMPLE 13

1-(2,3-Di-O-acetyl-5-chloro-5-deoxy-beta-L-ribofuranosyl)-5,6-dichloro-2-isopropylamino-1H-benzimidazole 2-Isopropylamino-5,6-dichlorobenzimidazole (0.52 g, 2.1 mmol), N,O-bis(trimethylsiyl) acetamide (0.58 m; 2.4 mmol), and 1,2-dichloroethane (20 mL) were combined and heated at 80° C., under nitrogen, for 20 min. The solution was cooled to rt and trimethysilyl triflate (0.27 mL, 1.4 mmol) was added. After 15 min., 1,2,3-tri-O-acetyl-5-chloro-5-deoxy-L-ribofuranose was added as a white sold. The solution was stirred under nitrogen at 80° C. for 3 h, then diluted with 1:3 hexanes:ethyl acetate (150 mL) and extracted with cold 10% aqueous sodium bicarbonate (2×50 mL). The organic layers were dried with anhydrous sodium sulfate, decanted, and evaporated. The crude residue was purified on a silica gel column (25×18 cm, 230–400 mesh) with (1:40) methanol:dichloromethane to give crude product (0.71 g). This material was fur purified by multiple cyclings on a chromatotron fitted with a 2 mm silica gel rotor, using (2:3) ethyl acete:hexane and (1:200) methanol:dichloromethane. Product was obtained as an off white solid (0.59 g, 1.2 mmol, 58%); $[\alpha]^{20}{}_D$=(−) 4.8 (c=0.5 DMF); MS (API+): m/z 478 (M+, 5.07).

Anal. Calcd. for $C_{19}H_{22}N_3O_5Cl_3 \cdot 0.60\ C_4H_8O_2 \cdot 0.50\ CH_2Cl_2$: C, 45.82; H, 4.88; N, 7.32 Found: C, 46.04; H, 4.71; N, 7.14.

EXAMPLE 14

2-tert-Butylamino-1-(5-Chloro-5-deoxy-beta-L-ribofuranosyl)-5,6-dichloro-1H-benzimidazole A solution of 2-tert-butylamino-1-(2,3-di-O-acetyl-5-chloro-5-deoxy-beta-L-ribofuranosyl)-5,6-dichloro-1H-benzimidazole(0.38 g, 0.77 mmol) in methanol (10 mL) and ethanol (10 mL) was combined with a solution of sodium carbonate (0.12 g, 1.2 mmol) in water (5 mL). The solution was stirred at rt for 18 h, then the methanol and ethanol were removed on the rotoevaporator. The solution was diluted with ethyl acetate (150 mL) and extracted with water (2×50 mL). The organics were dried, concentrated and purified on a chromatotron fitted with a 2 mm silica gel rotor, using 1:20 methanol:dichloromethane, to give a white solid (0.29 g, 0.71 mmol, 92%); m.p. 112–114° C.; $[\alpha]^{20}{}_D$=(+) 0.80 (c=0.5 DMF); UV $\lambda_{max}$ ($\epsilon$): pH 7.0: 304 nm (11,000), 276 (2,200), 261 (10,400), 246 (6,500); MS (API+): m/z (rel. intensity) 408 (31.50, M+); $^1$H NMR (DMSO-d$_6$) δ 7.63 (s, 1H, Ar—H), 7.51 (s, 1H, Ar—H), 6.21 (s, 1H, NH), 5.83 (d, 1H, H-1', J=7.5 Hz), 5.56 (d, 1H, OH, J=4.8 Hz), 5.46 (d, 1H, OH, J=7.8 Hz), 4.36 (apparent q, 1H, H-4, J=7.4 Hz), 4.18–4.02 (m, 4H, H-2', H-3' and H-5'), 1.51 (d, 9H, CH(CH$_3$)$_3$).

Anal. Calcd. for $C_{16}H_{20}N_3O_3Cl_3 \cdot 0.50\ H_2O$: C, 46.11; H, 5.05; N, 10.08. Found: C, 46.04; H, 5.02; N, 9.99.

EXAMPLE 15

2-tert-Butylamino-1-(2,3-di-O-acetyl-5-chloro-5-deoxy-beta-L-ribofuranosyl)-5,6-dichloro-1H-benzimidazole 2-tert-Butylamino-5,6-dichlorobenzimidazole (0.43 g, 1.6 mmol), N,O-bis(trimethylsiyl) acetamide (0.45 mL, 1.8 mmol), and 1,2-dichloroethane (20 mL) were combined and heated at 80° C., under nitrogen, for 20 min. The solution was cooled to rt and trimethylsilyl triflate (0.21 mL, 1.1 mmol) was added. After 15 min, 1,2,3 tri-O-acetyl-5-chloro-5-deoxy-L-ribofuranose was added as a white solid. The solution was stirred under nitrogen at 80° C. for 2–5 h, then diluted with 1:4 hexanes:ethyl acetate (150 mL) and extracted with cold 10% aqueous sodium bicarbonate (2×50 mL). The organic layers were dried with anhydrous sodium sulfate, decanted, and evaporated. The crude residue was purified on a silica gel column (25×16 cm, 230–400 mesh) with (1:100) acetone:dichloromethane to give an off white solid (0.42 g, 0.85 mmol 57%); $[\alpha]^{20}{}_D$=(−) 10.8 (c=0.5 DMF); MS (API+): m/z 492 (M+, 5.35).

Anal. Calcd. for $C_{20}H_{24}N_3O_5Cl_3 \cdot 0.50\ C_3H_6O \cdot 0.25\ CH_2Cl_2$: C, 48.11; H, 5.10; N, 7.74. Found: C, 48.19; H, 5.00; N, 7.57.

EXAMPLE 16

5,6-Dichloro-1-(3-deoxy-beta-L-ribofuranosyl)-2-isopropylamino-1H-benzimidazole

A solution of 1-(3-deoxy-2,5-di-O-acetyl-beta-L-ribofuranosyl)-5,6-dichloro-2-isopropylamino-1H-benzimidazole (0.36 g, 0.81 mmol) in methanol (10 mL) and ethanol (10 mL) was combined with a solution of sodium carbonate (0.13 g, 1.2 mmol) in water (3 mL). The solution was stirred at rt for 24 h, then the methanol and ethanol were removed an the rotoevaporator. The solution was diluted with ethyl acetate (120 mL) and extracted with sat'd NaCl (2×50 mL). The organics were dried (anhydrous sodium sulfate), concentrated and purified on a silica gel column (2.5×16 cm, 230–400 mesh) with 1:20 methanol:dichloromethane to give a white solid (0.21 g, 0.59 mmol, 79%); m.p. 153–155° C.; $[\alpha]^{20}{}_D$=(−) 32.8 (c=0.5 DMF); UV $\lambda_{max}$ ($\epsilon$): pH 7.0: 305 nm (11,300), 276 (2,000), 260 (9,300), 246 (6,400); MS (API+): m/z (rel. intensity) 360 (90.95, M+).

Anal. Calcd. for $C_{15}H_{19}N_3O_3Cl_2 \cdot 0.50\ H_2O$: C, 48.79; H, 5.46; N, 11.38. Found: C, 48.91; H, 5.39; N, 11.20.

EXAMPLE 17

1-(3-Deoxy-2,5-di-O-acetyl-beta-L-ribofuranosyl)-5,6-dichloro-2-isopropylamino-1H-benzimidazole 1-(3-Bromo-3-deoxy-2,5-di-O-acetyl-beta-L-xylofuranosyl)-5,6-dichloro-2-(isopropylamino-1H-benzimidazole 0.67 g, 1.3 mmol), tributyltin hydride, and AIBN were combined in anhydrous toluene. The solution was purged with nitrogen, then heated to 90° C. in an oil bath. After 2 h the solution was cooled to ambient temperature and diluted with acetonitrile (200 mL) and extracted with hexanes (3×50 mL). The acetonitrile layer was concentrated to give 0.53 g of crude product. This material was purified on a silica gel column (2.5×16 cm, 230–400 mesh) using (1:40) methanol:dichloromethane to give a white solid (0.41 g, 0.92 mmol, 72%); $[\alpha]^{20}{}_D$=(−) 26.4 (c=0.5 DMF); MS (API+): m/z (rel. intensity) 444 (21.63, M+).

Anal. Calcd. for $C_{19}H_{23}N_3O_5Cl_2$: C, 51.36; H 5.22; N, 9.46. Found. C, 51.50; H, 5.25; N, 9.28.

EXAMPLE 18

1-(3-Bromo-3-deoxy-2,5-di-O-acetyl-beta-L-xylofuranosyl)-5,6-dichloro-2-(isopropylamino)-1H-benzimidazole 5,6-Dichloro-2-isopropylamino-(beta-L-ribofuranosyl)-1H-benzimidazole (1.7 g, 4.5 mmol), triethyl orthoacetate, and tosic acid monohydrate, were combined in acetonitrile and stirred at ambient temperature for 18 h. The solution was treated with excess methanolic ammonia (ammonia was bubbled through 50 mL of cold methanol for 15 min). The resulting solids were filtered and washed with dichloromethane (100 mL). The filtrate and washings were concentrated to a yellow foam which was combine with acetyl bromide in 1,2-dichloromethane. The solution was heated in an 80° C. oil bath for 30 min, cooled, then poured into cold saturated $NaHCO_3$. This solution was extracted with dichloromethane (2×100 ml). The organics were dried (anhydrous sodium sulfate), decanted and concentrated to a yellow brown oil (3.1 g). Purification on a silica gel column (5×10 cm, 230–400 mesh) using (1:20) methanol: dichloromethane provided 2.5 g of crude material. Further purification on a silica gel column (5×14 cm, 230–400 mesh) using (1:50) acetone:dichloromethane provided pure product as an off white solid (0.86 g, 1.6 mmol, 36%): $[\alpha]^{20}{}_D$=(+) 14.8 (c=0.5 DMF); MS (API+): m/z (rel. intensity) 523 (100, $M^+$).

Anal. Calcd. for $C_{19}H_{22}N_3O_5Cl_2Br$. C, 43.62; H, 4.24; N, 8.03. Found: C, 43.79; H, 4.35; N, 7.87.

EXAMPLE 19

5,6-Dichloro-1-(2-deoxy-beta-L-erythro-pentofuranosyl)-2-isopropylamino-1H-benzimidazole A solution of 1-(2-deoxy-3,5-O-(1,1,3,3-tetraisopropyl)disiloxanyl-beta-L-erythropentofuranosyl)-5,6-dichloro-2-isopropylamino-1H-benzimidazole (0.25 g, 0.41 mmol) and tetrabutylammonium fluoride on silica gel (1.0 g) were combined in THF (8 mL). The solution was stirred at rt for 6 h, then filtered. The solids were washed with (1:9) methanol:dichloromethane and the filtrate and washings were concentrated and purified on a chromatotron fitted with a 2 mm silica gel rotor, using (1:20) methanol:dichloromethane. Product was obtained as a white solid after lyophiliztion (0.13 g, 0.36 mmol, 87%), m.p. 114–115° C. $[\alpha]^{20}{}_D$=(−) 43.6 (c=0.5 DMF); UV $\lambda_{max}$ (ε): pH 7.0:305 nm (11,300), 276 (2,000), 260 (9,400), 245 (6,300); MS (ESP+): m/z (rel. intensity) 360 (534, $M^+$).

Anal. Calcd. for $C_{15}H_{19}N_3O_3Cl_2.0.20\ H_2O.0.40\ CH_4O$: C, 49.11; H. 5.62; N, 11.16. Found. C, 49.21; H, 5.68; N, 11.01.

EXAMPLE 20

1-(2-Deoxy-3,5-O-(1,1,3-tetraisopropyl)disiloxanyl-beta-L-erythro-pentofuranosyl)-5,6-dichloro-2-isopropylamino-1H-benzimidazole 5,6-Dichloro-2-isopropylamino-1-2-phenoxythiocarbonyl-3,5-O-(1,1,3,3-tetraisopropyl)disiloxanyl-beta-L-ribofuranosyl)-1H-benzimidazole (0.51 g, 0.67 mmol) was combined with AIBN (0.011 g, 0.07 mmol), in toluene (20 mL) and the solution was purged with nitrogen. Tributyltin hydride (0.20 ml, 0.74 mmol) was added and the solution was heated in a 90° C. oil bath for 18 h. The reaction mixture was concentrated then dissolve in acetonitrile (100 ml) and extracted with hexanes (50 ml). The hexane layer was back-extracted with acetonitrile (3×100 ml). The combined acetonitrile layers were concentrated and purified on a silica gel column, (25×18 cm, 230–400 mesh) using (1:100) acetone:dichloromethane to give a white solid (0.34 g, 0.56 mmol, 83%); $[\alpha]^{20}{}_D$=(+) 17.0 (c=0.5 DMF); MS (ESP+): m/z (rel. intensity) 602 (69.52, $M^+$).

Anal. Calcd. for $C_{27}H_{45}N_3O_4CO_2Si_2.0.50\ H_2O$. C, 53.01; H, 758; N, 687. Found: C, 52.94; H, 7.38; N, 6.70.

EXAMPLE 21

5,6-Dichloro-2-isopropylamino-1-(2-phenoxythiocarbonyl-3,5-O-(1,1,3,3-tetraisopropyl) disiloxanyl-beta-L-ribofuranosyl)-1H-benzimidazole 5,6-Dichloro-2-isopropylamino-1-(3,5-O-(1,1,3,3-tetraisopropyl)disiloxanyl-beta-L-ribofuranosyl-1H-benzimidazole was combined with 4-(N,N-dimethylaminopyridine (0.46 g, 3.76 mmol) in acetonitrile (25 mL). Chloro phenyl thionocarbonate was added dropwise, and the solution was stirred at ambient temperature under $N_2$. After 18 h the solution was diluted with (1:1) hexane: ethyl acetate then extracted with saturated NaCl (2×50 mL). The organics were dried with anhydrous sodium sulfate and concentrated. The crude product was purified on a silica gel column (25×18 cm, 230–400 mesh) using (1:6) ethyl acetate:hexane. Pure product was obtained as a white solid (1.1 g, 1.4 mmol, 72%); $[\alpha]^{20}{}_D$=(+) 612 (c=0.5 DMF); MS (ESP+): m/z (rel. intensity) 754 (100, $M^+$).

Anal. Calcd. for $C_{34}H_{49}N_3O_6SCl_2Si_2.0.20\ C_6H_{14}$: C, 54.75; H, 6.76; N, 5.44. Found: C, 54.84; H, 6.72; N, 5.45.

EXAMPLE 22

5,6-Dichloro-2-(isopropylamino)-1-(3,5-O-(1,1,3,3-tetraisopropyl-1,3-disiloxanediyl-beta-L-ribofuranosyl-1H-benzimidazole 5,6-Dichloro-2-(isopropylamino)-1H-(beta-L-ribofuranosyl)-1H-benzimidazole (5.0 g, 13.3 mmol) was combined with 1,3-dichlor-1,1,3,3-tetraisopropyldisiloxane (4.6 ml, 14.6 mmol) and imidazole (3.6 g, 53.2 mmol) in DMF (14 mL). The solution was stirred under nitro at rt for 18 h. Water (160 mL) was added to the solution and the solids were filtered off. The solids were dissolved in 1:1 ethyl acetate:hexane (360 mL) and this solution was extracted with saturated NaCl (100 mL). The organics were dried with anhydrous sodium sulfate, decanted and concentrated. Crude product weighed 84 g and was purified on a silica gel column (5×16 cm, 230–400 mesh) with 1:100 methanol:dichloromethane to give 7.4 g of still crude material. Final purification on a Biotage Radial Compression Module (Biotage Inc., Charlottesville, Va.) with a 7.5×15 cm prepacked silica gel cartridge, provided pure product as a white solid (3.8 g, 6.3 mmol, 47%); m.p. 129–130° C.; $[\alpha]^{20}{}_D$=(+) 48.4 (c=0.5 DMF); MS (AP+): m/z (rel. intensity) 618 (100, $M^+$).

Anal. Calcd. for $C_{27}H_{45}N_3O_5Cl_2Si_2.0.25\ C_6H_{14}$: C, 53.46; H, 7.63; N, 6.56 Found: C, 53.55; H, 7.60; N, 6.74.

EXAMPLE 23

2-Bromo-5,6-dichloro-1-(2,3,5-tri-O-acetyl-beta-L-ribofuranosyl)-1H-benzimidazole From Bromination Reaction 5,6-Dichloro-1-(2,3,5-tri-O-acetyl-beta-L-ribofuranosyl)-1H-benzimidazole (1.0 g, 2.25 mmol) was combined with N-bromosuccinimide (0.88 g 4.94 mmol) in anhydrous 1,4-dioxane (50 mL). This solution was heated in an 80° C. oil bath for 15 min. The solution was cooled, diluted with ethyl acetate and extracted with 10% sodium bicarbonate (2×50 mL). The organics were dried with anhydrous $Na_2SO_4$, decanted and concentrated. The residue was purified on a silica gel column (5×11 cm, 230–400 mesh) with (1:50) methanol:dichloromethane to give a white solid which was identified as product by comparing it's $^1$H NMR to that of Example 1.

EXAMPLE 24

5,6-Dichloro-2-(isopropylamino)-1-(2,3,5-tri-O-acetyl-beta-L-ribofuranosyl)-1H-benzimidazole Anhydrous 1,2-dichloromethane (15 mL), 2-(isopropylamino)-5,6-dichlorobenzimidazole (5.9 mmol)), and N,O-bistrimethylsilylacetamide (11.8 mmol)) were combined and stirred at 80° C. for 30 min. Trimethylsilyl triflate (5.9 mmol)) was added and the solution was stirred at 80° C. for 45 min. Solid 1,2,3,4-tetra-O-acetyl-L-ribofuranoside (L-TAR) was added and stirring was continued at 80° C. for 3 h. More L-TAR was added (0.5 g, 1.6 mmol) at this time. After 1 hr the reaction was quenched with cold saturated t bicarbonate (40 mL), then extracted with dichloromethane (2×150 mL). The combined organics were dried (sodium sulfate), decanted, and concentrated to give 40 g of a gold solid. This material was purified on a silica gel column (5 cm×16 cm, 230 –400 mesh) with 1:30 methanol:dichloromethane to give an off white solid (2.21 g, 4.3 mmol, 73%); $[\alpha]^{20}_D$=(-) 28.4 (c=0.5 DMF).

Anal. Calcd. for $C_{22}H_{27}N_3O_7Cl_2$.1 $CH_4O$ C, 50.37; H, 5.70; N, 7.66. Found: C, 50.74; H, 5.41; N, 7.28.

General Procedure I: Synthesis of 2-(alkylamino)-1H-benzimidazoles Using 1-cyclohexyl-3-(2-morpholinoethyl) carbodiimide metho-p-toluenesulfonate as Desulfurizing Agent.

The appropriate 1,2-phenylenediamine is combined with the appropriate isothiocyanate (1.0–1.25 mmol/mmol of diamine) and anhydrous pyridine (3–5 mL/mmol of diamine). The resulting mixture is heated to 80° C. for 30 min, then 1-cyclohexyl-3-(2-morpholinoethyl)carbodiimide metho-p-toluenesulfonate (1.1–1.35 mmol/mmol of diamine) is added as a solid in one portion. The resulting mixture is allowed to stir at 80–90° C. for 3–20 h, after which time it is allowed to cool to room temperature. The remainder of the procedure is the same as for example X, except that the product is purified either by silica gel chromatography or by recrystallization from either acetonitrile or 1,4-dioxane.

General Procedure II: Coupling of 2-(alkylamino)-1H-benzimidazoles with 1,2,3,5-tri-O-acetyl-ribofuranose The appropriate 2-(alkylamino)-1H-benzimidazole was combined with 1,2-dichloroethane (2–3 mL/mmol of benzimidazole) and N,O-bis(methylsilyl)acetamide (1–1.25 mmol/mmol of benzimidazole) and the resulting mixture was heated to 80° C. for 30 min. Trimethylsilyl trifluoromethanesulfonate (0.5–0.7 mmol/mmol of benzimidazole) was added and the mixture was allowed to stirred at 80° C. for an additional 15 min, after which time 1,2,3,5-tetra-O-acetyl-L-ribofuranose (1–1.25 mmol/mmol of benzimidazole) was added as a solid in one portion. The resulting mixture was allowed to stir at 80° C. for 2–20 h, after which time it was allowed to cool to room temperature. It was then diluted with 5% aqueous sodium bicarbonate (10 mL/mmol of benzimidazole) and dichloromethane (35 mL/mmol of benzimidazole) and the two-phase mixture was stirred at room temperature for 30 min. The organic layer was collected and the aqueous layer was backextracted with an additional portion of dichloromethane (3–5 mL/mmol of benzimidazole) and the combined organic layers were dried over magnesium sulfate, filtered and the solvents were removed under reduced pressure using a rotary evaporator. The products were further purified by silica gel chromatography.

General Procedure III: Deprotection of 2-(alkylamino)-1-(2,3,5-tri-O-acetyl-beta-L-ribofuranosyl-1H-benzimidazoles The appropriate 2-(alkylamino)-1-(2,3,5-tri-O-acetyl-beta-L-ribofuranosyl)-1H-benzimidazole was dissolved in ethanol (4–5 mL/mmol of triacetate). Into a separate flask were placed sodium carbonate (1.0–1.3 mmol/mmol of triacetate), water (1–2 mL/mmol of triacetate), and methanol (3 mL/mmol of triacetate). The sodium carbonate suspension was added to the ethanolic solution of the triacetate at room temperature and in one portion. The resulting mixture was allowed to stir at room temperature for 18 h. The mixture was then diluted with ethyl acetate (25 mL/mmol of triacetate). The organic layer was collected and was washed with saturated aqueous brine (100 mL/mmol of triacetate), dried over magnesium sulfate, filtered, and the solvents were removed by rotary evaporation. The products were further purified by silica gel chromatography.

EXAMPLE 25

5,6-Dichloro-2-(isopropylamino)-1-benzimidazole 5,6-Dichloro-1,2-phenylenediamine (200.0 g, 1.13 mol), isopropyl isothiocyanate (122.0 g, 1.21 mol), 1-cyclohexyl-3-(2-morpholinoethyl)carbodiimide metho-p-toluenesulfonate (622.0 g, 1.47 mol) and pyridine (4 L) were used according to general procedure I. The product was recrystallized from acetonitrile to give 184 g (67%) of a brown solid. Analytical data were consistent with those reported above.

EXAMPLE 26

2-(Cyclopropylamino)-5,6-dichloro-1H-benzimidazole 4,5-Dichloro-1,2-phenylenediamine (6.04 g, 34.1 mmol), cyclopropyl isothiocyanate (3.69 g, 37.2 mmol), 1-cyclohexyl-3-(2-morpholinoethyl)carbodiimide metho-p-toluenesulfonate (20.1 g, 47.4 mmol) and pyridine (135 mL) were used according to general procedure I. The product was recrystallized from acetonitrile to afford 5.82 g (70%) of a yellow solid; m.p. 223–225° C. Anal. Calcd. for $C_{10}H_9Cl_2N_3$: C, 49.61; H, 3.75; N, 17.36. Found: C, 49.53; H, 3.78; N, 17.12.

EXAMPLE 27

2,34-Trichloronitroaniline 4,5-Dichloro-2-nitroaniline (15.2 g, 73.2 mmol), N-chlorosuccinimide (12.2 g, 91.6 mmol) and N,N-dimethylformamide (150 mL) were combined and the resulting orange solution was heated to 100° C. for 1 h. The solution was allowed to cool to room temperature and was poured into a flask containing ice water (1.2 L). The yellow solid was collected and was dissolved in dichloromethane (1.5 L), resulting in two-phases. The organic layer was collected and was dried over magnesium sulfate, filtered and the solvents were removed under reduced pressure by rotary evaporation to leave 17.6 g (98%) of a yellow solid. MS (CI): m/z 239.

EXAMPLE 28

3,4-Trichloro-1,2-phenylenediamine

6-Nitro-2,3,4-trichloroaniline (17.6 g, 72.8 mmol), iron powder (140 g, 250 mmol), and ethanol (400 mL) were combined and the resulting suspension was cooled to 0° C. Concentrated hydrochloric acid (37%, 93 mL, 1.14 mol) was added dropwise over a period of 15 min by means of an addition funnel. When the addition was complete, the resulting suspension was heated to reflux for 35 h, after which time it was allowed to cool to room temperature and was subsequently diluted with water (2 L). The pH of the mixture was adjusted to approximately 8 by the slow addition of sodium carbonate. The product was extracted with ethyl acetate (2 L), dried over magnesium sulfate and the solvents were removed under reduced pressure by rotary evaporation The product was further purified by silica gel chromatography using 65:35 hexane/ethyl acetate to afford 10.9 g (72%) of a tan solid, m.p. 113 115° C. Anal. Calcd. for $C_6H_{15}C_3N_2$: C, 34.08; H, 2:38; N, 13.25. Found. C, 34.14; H, 2.41; N, 13.18.

EXAMPLE 29

2-(Isopropylamino)-4,5,6-trichloro-1H-benzimidazole 3,4,5-Trichloro-1,2-phenylenediamine (3.12 g, 14.8 mmol), isopropyl isothiocyanate (1.62 g, 16.0 mmol), 1-cyclohexyl-3-2-morpholinoethyl)carbodiimide metho-p-toluenesulfonate (8.4 g, 19.9 mmol), and pyridine (50 mL) were used according to general procedure II. The product was recrystallized from 1,4-dioxane to give 2.9 g (72%) of a tan solid. MS (CI): m/z 276 (M+1). Anal. Calcd. for $C_{10}H_{10}Cl_3N_3$-(0.10 $C_4H_8O_2$): C, 43.47; H, 3.79; N, 14.62. Found. C, 43.70; H, 3.89; N, 14.43.

EXAMPLE 30

2-(Isopropylamino)-4,5,6-trichloro-1-(2,3,5-tri-O-acetyl-beta-L-ribofuranosyl-1-benzimidazole 2-Isopropylamino)-4,5,6-trichloro-1H-benzimidazole (1.15 g, 4.00 mmol), N,O-bis(trimethylsilyl)acetamide (0.7 mL, 0.58 g, 2.83 mmol), trimethylsilyl trifluoromethanesulfonate (0.5 ml, 0.58 g, 2.59 mmol), 1,2,3,5-tetra-O-acetyl-L-ribofuranoside (1.50 g, 4.71 mmol) and 1,2-dichloromethane (10 mL) were used according to general procedure II. The product was isolated by silica gel chromatography using 60:1 dichloromethane/methanol to afford 1.05 g (49%) of a yellow foam. MS (CI): m/z 536 (M+1).

EXAMPLE 31

2-(Isopropylamino)-4,5,6-trichloro-1-(beta-L-ribofuranosyl)-1H-benzimidazole 2-(Isopropylamino)-4,5,6-trichloro-1-(2,3,5-triacetyl-beta-L-ribofuranosyl)-1H-benzimidazole (1.00 g, 1.86 mmol), sodium carbonate (0.26 g, 2.45 mmol), water (4 mL), methanol (6 mL) and ethanol (8 mL) were used according to general procedure III. The product was purified by silica gel chromatography using 10:1 dichloromethane/methanol to afford 0.57 g (75%) of a white powder; m.p. 223–224° C. Anal. Calcd. for $C_{15}H_{18}Cl_3N_3O_4$: C, 43.87; H, 4.42; N, 10.23. Found. C, 43.63; H, 4.55; N, 9.98.

EXAMPLE 32

2-(Cyclopropylamino)-4,5,6-trichloro-1H-benzimidazole 3,4,5-Trichloro-1,2-phenylenediamine (3.02 g, 14.28 mmol), cyclopropyl isothiocyanate (1.53 g, 15.42 mmol), 1-cyclohexyl-3-(2-morpholinoethyl)carbodiimide metho-p-toluenesulfonate (8.24 g, 19.45 mmol) and pyridine (55 mL) were used according to general procedure I. The product was recrystallized from 1,4-dioxane to afford 3.29 g (83%) of a white solid. MS (CI): m/z 274. Anal. Calcd for $C_{10}H_8Cl_3N_3$-(0.6 $C_4H_8O_2$): C, 45.21; H, 3.92; N, 12.76. Found C, 45.37; H, 3.91; N, 12.76.

EXAMPLE 33

2(Cyclopropylamino)-4,5,6-trichloro-1-(2,3,5-tri-O-acetyl-beta-L-ribofuranosyl)-1H-benzimidazole 2-Cyclopropylamino)-4,5,6-trichloro-1H-benzimidazole (1.32 g, 4.00 mmol), N,O-bis(trimethylsilyl)acetamide (1.0 mL, 0.82 g, 4.05 mmol), trimethylsilyl trifluoromethanesulfonate (0.5 mL, 0.58 g, 2.59 mmol), 1,2,3,-tetra-O-acetyl-L-ribofuranose (1.70 g, 5.34 mmol) and 1,2-dichloromethane (12 mL) were used according to general procedure II. The product was purified by silica gel chromatography using 60:1 dichloromethane/methanol to afford 1.11 g (52%) of a yellow foam. MS (CI): m/z 534 (M+1).

EXAMPLE 34

2-(Cyclopropylamino)-4,5,6-trichloro-1-beta-L-ribofuranosyl)-1H-benzimidazole 2-Cyclopropylamino)-4,5,6-trichloro-1,2,3-tri-O-acetyl-beta-L-ribofuranosyl-1H-benzimidazole (1.11 g, 2.08 mmol), sodium carbonate (0.29 g, 2.77 mmol), water (4 mL), methanol (6 mL), and ethanol (8 mL) were used according to general procedure III. The product was purified by silica gel chromatography using 10:1 dichloromethane/methanol to afford 0.47 g (56%) of a white powder; m.p. 208–209° C. Anal. Calcd. for $C_{15}H_{16}Cl_3N_3O_4$: C, 44.09; H, 3.95; N, 10.28. Found: C, 44.14; H, 3.98; N, 10.18.

EXAMPLE 35

2-Bromo-3,4-dichloro-6-nitroaniline 4,5-Dichloro-2-nitroaniline (41.0 g, 1.98 mmol), N-bromosuccinimide (42.86 g, 2.41 mmol) and N,N-dimethylformamide were combined and heated to 100° C. for 1 h. The mixture was allowed to cool to room temperature and was poured into a flask containing ice water (1 L). The yellow solid was collected and was dissolved in dichloromethane (2 L), resulting in two phases. The organic layer was collected and was dried over magnesium sulfate, filtered and the solvents were removed under reduced pressure using a rotary evaporator to leave 48.62 g (86%) of a brown solid. Anal. Calcd. for $C_6H_3BrCl_2N_2O_2$: C, 25.21; H, 1.06; N, 9.80. Found: C, 25.32; H, 1.13; N, 9.68.

EXAMPLE 36

3-Bromo-4,5-dichloro-1,2-phenylenediamine

2-Bromo-3,4-dichloronitroaniline (48.3 g, 168.9 mmol), iron powder (30.0 g, 537.2 mmol) and ethanol (1 L) were combined and the resulting suspension was cooled to 0° C. Concentrated hydrochloric add (37%, 193.0 mL, 2.36 mol) was then added dropwise over 15 min by means of an addition funnel. The resulting mixture was heated to reflux for 1 h, after which time it was allowed to cool to room temperature. The mixture was diluted with water (15 L) and the pH was adjusted to approximately 8 by the addition of sodium carbonate. The product was extracted with ethyl acetate (1 L), dried over magnesium sulfate, filtered and the solvents were removed under reduced pressure using a rotary evaporator. The product was crystallized from a methanol/water mixture to afford 34.21 g (79%) of a brown solid; m.p. 128–129° C. Anal. Calcd for $C_6H_5BrCl_2N_2$: C, 28.16; H, 1.97; N, 10.95. Found: C, 28.29; H, 1.96; N, 10:79.

EXAMPLE 37

4-Bromo-5,6-dichloro-2-(isopropylamino-1H-benzimidazole

3-Bromo-4-chloro-1,2-phenylenediamine (25.0 g, 97.7 mmol), isopropyl isothiocyanate (11.2 g, 110.5 mmol), 1-cyclohexyl-3-(2-morpholinoethyl)carbodiimide metho-p-toluenesulfonate (56.8 g, 134.1 mmol) and pyridine (500 mL) were used according to general procedure I. The product was isolated by silica gel chromatography using 7:3 hexane/ethyl acetate to afford 19.2 g (62%/) of a tan solid, m.p. 247–249° C. Anal. Calcd for $C_{10}H_{10}BrCl_2N_3$-(0.08 $C_6H_{14}$): C, 38.15; H, 3.40; N, 12.74. Found. C, 38.15; H, 3.39; N, 12.77.

EXAMPLE 38

4-Bromo-5,6-dichloro-2-(isopropylamino)-1-(2,3,5-tri-O-acetyl-beta-L-ribofuranosyl)-1H-benzimidazole 4-Bromo-5,6-dichloro-1-(isopropylamino)-1H-benzimidazole (1.33 g, 4.03 mmol), N,O-bis(trimethylsilyl) acetamide (1.0 mL, 0.82 g, 4.05 mmol), trimethylsilyl trifluoromethanesulfonate (0.5 mL, 0.58 g, 2.59 mmol), 1,2,3,5-tetra-O-acetyl-L-ribofuranoside (1.69 g, 5.31 mmol) and 1,2-dichloroethane (12 mL) were used according to general procedure II. The product was isolated by silica gel chromatography using 60:1 dichloromethane/methanol to afford 1.16 g (50%) of a yellow foam. MS (CI): m/z 580 (M+1).

EXAMPLE 39

4-Bromo-5,6-dichloro-2-(isopropylamino)-1-(beta-L-ribofuranosyl)-1H-benzimidazole 4-Bromo-5,6-dichloro-2-(isopropylamino)-1-(2,3,5-tri-O-acetyl-beta-L-ribofuranosyl)-1H-benzimidazole (1.16 g, 2.0 mmol), sodium carbonate (0.28 g, 2.64 mmol), water (4 mL), methanol (6 mL), and ethanol (8 mL) were used according to general procedure III. The product was purified by silica gel chromatography using 10:1 dichloromethane/methanol to afford 0.64 g (70%) of a white powder; m.p. 221–222° C. Anal. Calcd for $C_{15}H_{18}BrCl_2N_3O_4$: C, 39.59; H, 3.99; N, 9.23. Found: C, 39.42; H, 4.20; N, 9.05.

EXAMPLE 40

4-Bromo-2-(cyclopropylamino)-5,6-dichloro-1H-benzimidazole

3-Bromo-4,5-dichloro-1,2-phenylenediamine (5.12 g, 20.0 mmol), cyclopropyl isothiocyanate (2.18 g, 21.98 mmol), 1-cyclohexyl-3-(2-morpholinoethylcarbodiimide metho-p-toluenesulfonate (11.0 g, 25.97 mmol) and pyridine (75 mL) were used according to general procedure I. The product was recrystallized from 1,4-dioxane to afford 2.23 g (53%) of a white solid. MS (CI): m/z 319 amu. Anal. Calcd for $C_{10}H_8BrCl_2N_3$(0.35 $C_4H_8O_2$): C, 38.92; H, 3.09; N, 11.94. Found: C, 39.17; H, 3.05; N, 11.94.

EXAMPLE 41

4-Bromo-2-(cyclpropylamino)-5,6-dichloro-1-(2,3,5-tri-O-acetyl-beta-L-ribofuranosyl)-1H-benzimidazole 4-Bromo-2-cyclopropylamino)-5,6-dichloro-1H-benzimidazole (1.40 g, 3.98 mmol), N,O-bis(trimethylsilyl) acetamide (1.0 mL, 0.82 g, 4.05 mmol), trimethylsilyl trifluoromethanesulfonate (0.5 mL, 0.58 g, 2.59 mmol), 1,2,3,5-tetra-O-acetyl-L-ribofuranoside (1.68 g, 5.28 mmol) and 1,2-dichloroethane (12 mL) were used according to general procedure II. The product was purified by silica gel chromatography using 60:1 dichloromethane/methanol to afford 1.01 g (45%) of a yellow foam. MS (CI): m/z 578 (M+1).

EXAMPLE 42

4-Bromo-(cyclopropylamino)-5,6-dichloro-1-(beta-L-ribofuranosyl)-1H-benzimidazole 4-Bromo-2-cyclopropylamino)-5,6-dichloro-1-(2,3,5-tri-O-acetyl-beta-L-ribofuranosyl)-1H benzimidazole (1.01 g, 1.74 mmol), sodium carbonate (0.265 g, 2.50 mmol), water (4 mL), methanol (5 mL), and ethanol (8 mL) were used according to general procedure III. The product was purified using silica gel chromatography using 10.1 dichloromethane/methanol to afford 0.28 g (36%) of a white solid: m.p. 205–208° C. Anal. calcd for $C_{15}H_{16}O_2BrN_3O_4$-(0.25 $C_4H_7O_2$): C, 40.45; H, 3.82; N, 8.84. Found: C, 4.38, H, 3.95; N, 8.90.

EXAMPLE 43

4,5-Difluoro-1,2-phenylenediamine

Into a Parr bottle were placed 4,5-difluoro-2-nitroanilne (5.00 g, 28.72 mmol), platinum (IV) oxide (0.31 g, 1.13 mmol) and methanol (60 mL). The bottle was flushed three times with hydrogen and was finally pressurized to 45 psig with hydrogen. The bottle was shaken for 5 h, after which time it was depressurized and the contents were poured into a separatory funnel containing ethyl acetate (300 mL) and water (300 mL). The organic layer was collected and washed with saturated aqueous brine solution (100 mL), dried over magnesium sulfate and the solvents were removed under reduced pressure using a rotary evaporator to leave 3.37 g (81%) of a brown solid. MS (CI): m/z 145 (M+1).

EXAMPLE 44

5,6-Difluoro-2-(isopropylamino)-1H-benzimidazole 4,5-Difluoro-1,2-phenylenediamine (2.87 g, 19.91 mmol), isopropyl isothiocyanate (2.19 g, 21.65 mmol), 1-cyclohexyl-3-(2-morpholinoethyl)carbodiimide metho-p-toluenesulfonate (11.38 g, 26.87 mmol) and pyridine (75 mL) were used according to general method I. The product was recrystallized from 1,4-dioxane to afford 2.23 g (53%) of a white solid; m.p. 188–189° C. Anal. Calcd for $C_{10}H_{11}F_2N_3$: C, 56.87; A, 5.25; N, 19.89. Found C, 56.95; H, 5.25; N, 19.98.

EXAMPLE 45

5,6-Difluoro-2-(isopropylamino)-1-(2,3,5-tri-O-acetyl-beta-L-ribofuranosyl)-1H-benzimidazole 5,6-Difluoro-2-isopropylamino)-1H-benzimidazole (0.84 g, 4.00 mmol), N,O-bis(trimethylsilyl)acetamide (0.70 mL, 0.58 g, 2.83 mmol), trimethylsilyl trifluoromethanesulfonate (0.5 mL, 0.58 g, 2.60 mmol), 1,2,3,5-tetra-O-acetyl-L-ribofuranoside (1.50 g, 4.71 mmol) and 1,2-dichloroethane (9 mL) were used according to general procedure II. The product was purified by silica gel chromatography using 35:1 dichloromethane/methanol to afford 1.33 g (70%) of a yellow foam. MS (CI): m/z 470 (M+1).

EXAMPLE 46

5,6-Difluoro-2-(isopropylamino)-1-(beta-L-ribofuranosyl)-1H-benzimidazole 5,6-Difluoro-2-(isopropylamino)-1,2,3,5-tri-O-acetyl-beta-L-ribofuranosyl)-1H-benzimidazole (1.33 g, 2.3 mmol), sodium carbonate (0.31 g, 2.92 mmol), water (5 mL), methanol (10 mL), and ethanol (15 mL) were used according to general procedure III. The product was purified by silica gel chromatography using 10:1 dichloromethane/methanol to afford 0.52 g (53%) of a white solid; m.p. 156–158° C. Anal. Calcd for $C_{15}H_{19}F_2N_3O_4$: C, 52.48; H, 5.58; N, 12.24. Found: C, 52.23; H, 5.63; N, 12.15.

EXAMPLE 47

3-Chloro-1,2-phenylenediamine

2-Chloronitroaniline (14.10 g, 81.71 mmol), Raney-nickel (5.02 g of a 50% slurry in water), and ethanol (200 mL) were combined in an autoclave which was pressurized to 150 psig with hydrogen. The resulting mixture was allowed to stir overnight at RT. The mixture was then filtered through a pad of celite, which was subsequently washed with several portions of methanol, and the solvents were removed by rotatry evaporation to afford 10.43 g (89%) of a viscous, brown oil, which darkened upon standing. MS (EI): m/z 143.1 (M+H).

EXAMPLE 48

4-Chloro-2-(isopropylamino)-1H-benzimidazole

3-Chloro-1,2-phenylenediamine (6.41 g, 44.95 mmol), isopropyl isothiocyanate (5.20 g, 51.6 mmol), 1-cyclohexyl-3-(2-morpholinoethyl)carbodiimide metho-p-toluenesulfonate (25.0 g, 59.02 mmol) and pyridine (300 mL) were used according to general procedure I. The product was recrystallized from 1,4-dioxane afford 5.45 g (58%) of a brownish solid. MS (EI): m/z 210.1 (M+H). Anal. calcd for $C_{10}H_{12}ClN_3$-(0.5 $C_4H_8O_2$): C, 56.80; H, 6.36; N, 16.56. Found: C, 57.00; H, 6.34; N, 16.69.

EXAMPLE 49

4-Chloro-2-(isopropylamino)-1-(2,3,5-tri-O-acetyl-beta-L-ribofuranosyl)-1H-benzimidazole 4-Chloro-2-(isopropylamino)-1H-benzimidazole (2.24 g, 10.68 mmol), N,O-bis(trimethylsilyl)acetamide (3.00 mL, 2.47g, 12.14 mmol), trimethylsilyl trifluoromethanesulfonate (1.2 mL, 1.42 g, 6.00 mmol), 1,2,3,5-tetra-O-acetyl-L-ribofuranose (4.46 g, 14.01 mmol) and 1,2-dichloroethane (35 mL) were used according to general procedure II. The product was purified by silica gel chromatography using 95:5 dichloromethane/acetonitrile to afford 2.34 g (47%) of an off-white foam MS (EI): m/z 468.2 (M+H).

EXAMPLE 50

4-Chloro-2-(isopropylamino)-1-(beta-L-ribofuranosyl)-1H-benzimidazole

4-Chloro-2-(isopropylamino)-1-(2,3,5-tri-O-acetyl-beta-L-ribofuranosyl)-1H-benzimidazole (2.24 g, 4.79 mmol), sodium carbonate (0.67 g, 6.32 mmol), water (7 mL), methanol (14 mL) and ethanol (20 mL) were used according to general procedure III. The product was purified by silica gel chromatography using 10:1 dichloromethane/methanol to afford 1.12 g (68%) of a white solid: m.p. 225–227° C. Anal. calcd for $C_{15}H_{20}ClN_3O_4$: C, 52.77; H, 5.91; N, 12.32. Found: C, 52.79; H, 5.96; N, 12.25.

EXAMPLE 51

4,6-Dichloro-2-(isopropylamino)-1H-benzimidazole 3,5-Dichloro-1,2-phenylenediamine (1.30 g, 7.32 mmol), isopropyl isothiocyanate (0.81 g, 8.00 mmol), 1-cyclohexyl-1-3-(2-morpholinoethyl)carbodiimide metho-p-toluenesulfonate (4.19 g, 9.89 mmol) and pyridine (25 mL) were used according to general procedure I. The product was recrystallized from 1,4-dioxane to afford 1.07 g (60%) of a white solid. Anal. calcd for $C_{10}H_{11}Cl_{12}N_3$-(0.25 $C_4H_8O_2$): C, 49.64; H, 4.92; N, 15.79. Found: C, 49.54; H, 4.94; N, 15.79.

EXAMPLE 52

4,6-Dichloro-2-(isopropylamino)-1-(2,3,5-tri-O-acetyl-beta-ribofuranosyl)-1H-benzimidazole 4-Dichloro-2-(isopropylamino)-1H-benzimidazole (0.83 g, 3.40 mmol), N,O-bis(trimethylsilyl)acetamide (0.88 mL, 0.72 g, 3.56 mmol), trimethylsilyl trifluoromethanesulfonate (0.43 mL, 0.49 g, 2.20 mmol), 1,2,3,5-tetra-O-acetyl-ribofuranose (1.31 g, 4.12 mmol) and 1,2-dichloroethane (10 mL) were used according to general procedure II. The product was purified by silica gel chromatography using 60.1 dichloromethane/methanol to afford 0.63 g (37%) of a white foam. MS (CI): m/z 502.1 (M+H).

EXAMPLE 53

4,6-Dichloro-2-(isopropylamino)-1-(beta-L-ribofuranosyl)-1H-benzimidazole 4,6-Dichloro-2-(isopropylamino)-1-2,3,5tri-O-acetyl-beta-L-ribofuranosyl)-1H-benzimidazole (0.63 g, 1.26 mmol), sodium carbonate (0.19 g, 1.82 mmol), water (3 mL), methanol (4 mL), and ethanol (6 mL) were used according to general procedure III. The product was purified by silica gel chromatography using 10:1 dichloromethane/methanol to afford 0.33 g (70%) of a white solid. m.p. 212–214° C. Anal. calcd for $C_{15}H_{19}Cl_2N_3O_4$: C, 47.89; H, 5.09; N, 11.17. Found: C, 47.79; H, 5.14; N, 11.09.

EXAMPLE 54

1,2,3-tri-O-acetyl-L-erythro-pentofuranoside

L-Erythrose (5.0 g, 41.6 mmol), prepared from L-erythruronolactone according to the method of Hudlicky et al. (Journal of Organic Chemistry, 1990, 55, 4683), was combined with pyridine (150 mL). 4-Dimethylaminopyridine (0.20 g, 1.67 mmol) and acetic anhydride (23.61 mL, 25.50 g, 24.95 mmol) were added at room temperature and the mixture was allowed to stir for 3 h. It was then poured into a flask containing saturated aqueous sodium bicarbonate solution (100 mL). The product was extracted with dichloromethane (500 mL) and the solvents were removed under reduced pressure using a rotary evaporator. The remaining residue was dissolved in ethyl acetate (500 mL) and was washed with 0.1 N hydrochloric add (200 mL) and the solvents were again removed under reduced pressure. The product was purified by silica gel chromatography using 3:1 hexane/ethyl acetate to afford 4.35 g (42%) of a yellow oil. Anal. Calcd for $C_{10}H_{14}O_7$. C, 48.8; H, 5.73. Found C, 49.14; H, 5.85.

EXAMPLE 55

5,6-Dichloro-2-(isopropylamino)-1-(2,3-di-O-acetyl-beta-L-erythro-pentofuranosyl)-1H-benzimidazole 5,6-Dichloro-2-(isopropylamino)-1H-benzimidazole (1.00 g, 4.09 mmol), N,O-bis(trimethylsilyl)acetamide (1.06 mL, 0.87 g, 4.29 mmol), trimethylsilyl trifluoromethanesulfonate (0.51 mL, 0.59 g, 2.66 mmol), 1,2,3-tri-O-acetyl-L-erythro-pentofuranoside (1.10 g, 4.49 mmol) and 1,2-dichloroethane (25 mL) were used according to general procedure II. The product was purified by silica gel chromatography using 30:1 dichloromethane/methanol to afford 0.45 g (26%) of a brown solid; m.p. 59–63° C. MS (CI): m/z 430 (M+1).

EXAMPLE 56

5,6-Dichloro-2-(isopropylamino)-1-beta-L-erythro-pentofuranosyl)-1H-benzimidazole 5,6-Dichloro-2-(isopropylamino)-1-(2,3-di-O-acetyl-beta-L-erythro-pentofuranosyl)-1H-benzimidazole (0.34 g, 0.79 mmol), sodium carbonate (0.13 g, 1.23 mmol), water (3 mL), methanol (3 mL), and ethanol (10 mL) were used according to general procedure III. After removal of the solvents under reduced pressure, the material (0.17 g 63%) was found to be analytically pure and did not require any further purification; m.p. 180–181° C. Anal. Calcd for $C_{14}H_{17}C_2N_3O_3$: C, 48.57; H, 4.95; N, 12.14. Found: C, 48.33; H. 4.89; N, 11.97.

EXAMPLE 57

2-(Isopropylamino)-4,5,6-trichloro-1-(2,3-di-O-acetyl-beta-L-erythro-pentafuranosyl)-1H-benzimidazole 2-(Isopropylamino)-4,5,6-trichloro-1H-benzimidazole (0.86 g, 3.10 mmol), N,O-bis(trimethylsilyl)acetamide (0.80 ml, 0.66 g, 3.26 mmol), trimethylsilyl trifluoromethanesulfonate (0.39 mL, 0.45 g, 2.01 mmol), 1,2,3-tri-O-acetyl-L-erythro-pentofuranoside (0.84 g, 3.41 mmol) and 1,2-dichloroethane (25 mL) were used according to general procedure II. The product was purified by silica gel chromatography using 60:1 dichloromethane/methanol to afford 0.28 g (20%) of a white foam. MS (CI): m/z 464.1 (M+H).

EXAMPLE 58

2-(Isopropylamino)-4,5,6-trichloro-1-(beta-L-erythro-pentofuranosyl)-1H-benzimidazole 2-(Isopropylamino)-4,5,6-trichloro-1-(2,3-di-acetyl-beta-L-erythro-pentofuranoside (0.05 g, 0.12 mmol), sodium carbonate (0.02 g, 0.17 mmol), water (3 mL), methanol (3 mL), and ethanol (5 mL) were used according to general procedure III. The product was purified using 98:2 dichloromethane/methanol to afford 0.04 g (91%) of a white solid: m.p. 199–200° C. (dec). Anal. calcd for $C_{14}H_{16}Cl_3N_3O_3$. C, 44.32; H, 4.25; N, 11.08. Found: C, 44.34; H, 4.30; N, 10.89.

EXAMPLE 59

3,4-Dichloro-1,2-phenylenediamine 2,3-Dichloro-6-nitroaniline (20.11 g, 97.14 mmol), Raney-nickel (4.78 g of a 50% slurry in water), and ethanol (250 mL) were combined in an autoclave which was pressurized to 150 psig with hydrogen The resulting reaction mixture was allowed to stir at RT overnight. The mixture was then filtered through a pad of celite, which was subsequently washed with several portions of methanol, and the solvents were removed by rotary evaporation to leave a dark brown solid. The solid was slurried and in hexanes and was collected on a Büchner funnel to afford 16.31 g (95%) of a brown solid. MS (EI): m/z 177.0 (M+H).

EXAMPLE 60

3,4-Dichloro-2-(isopropylamino)-1H-benzimidazole 3,4-Dichloro-1,2-phenylenediamine (8.00 g, 45.19 mmol), isopropyl isothiocyanate (5.26 g, 51.99 mmol), cyclohexyl-3(2-morpholinoethyl)carbodiimide metho-p-toluenesulfonate (25.0, 59.02 mmol), and pyridine (250 mL) were used according to general procedure I. The product was recrystallized from 1,4-dioxane to afford 6.12 g (55%/) of a white solid. MS (EI): m/z 244 (M+H). Anal. calcd for $C_{10}H_{11}Cl_2N_3$-(0.35 $C_4H_8O_2$): C, 49.80; H, 5.06; N, 15.28. Found: C, 49.95; H, 5.05; N, 15.08.

EXAMPLE 61

3,4-Dichloro-2-isopropylamino)-1-(2,3,5-tri-O-acetyl-beta-L-ribofuranosyl)-1H-benzimidazole 3,4-Dichloro-2-(isopropylamino)-1H-benzimidazole (2.0 g, 7.31 mmol), N,O-bis(trimethylsilyl)acetamide (2.0 mL, 1.65 g, 8.09 mmol), trimethylsilyl trifluoromethanesulfonate (0.9 mL, 1.06 g, 4.50 mmol), 1,2,3,5-tetra-O-acetyl-beta-L-ribofuranose (3.03 g, 9.52 mmol) and 1,2-dichloroethane (35 mL) were used according to general procedure II. The product was purified by silica gel chromatography using 95:5 dichloromethane/acetonitrile to afford 2.08 g (56%) of a yellow foam MS (EI): m/z 502.0 (M+H).

EXAMPLE 62

3,4-Dichloro-2-(isopropylamino)-1-(beta-L-ribofuranosyl)-1H-benzimidazole 3,4-Dichloro-2-(isopropylamino)-1-(2,3,5-acetyl-beta-L-ribofuranosyl)-1H-benzimidazole 2.06 g, 4.10 mmol), sodium carbonate (0.60 g, 5.66 mmol), water (12 mL), methanol (10 mL), and ethanol (24 mL) were used according to general procedure III. The product was purified by silica gel chromatography using 10:1 dichloromethane/methanol to afford a white solid.

EXAMPLE 63

Human Cytomegalovirus (HCMV) Assay

HCMV strain AD169 was grown on monolayers of human embryonic lung cells (MRC5 cells) in 96 well plates. After infection of the cells at a ratio of approximately 0.01 infectious virus particals per cell, the compounds to be tested were added to selected wells at six different concentrations, each in triplicate The same concentrations of compound were also applied to wells containing monolayers of uninfected cells in order to assess compound cytotoxicity. The plates were incubated for 5 days, and the minimum cytotoxic dose was estimated from microscopic examination. The IC50 for antiviral effect was estimated from measurements of HCMV DNA in each well by blotting and quantitative specific DNA hybridization, similar to the method of Gadler. (Antimicrob. Agents Chemother. 1983, 24, 370–374).

| Example | HCMV IC50 | MRC5 tox CC50 |
|---|---|---|
| Example 1 | 2.1 μM | 100 μM |
| Example 3 | 0.6 μM | 30 μM |
| Example 12 | 1.4 μM | 30 μM |
| Example 14 | 1.0 μM | 30 μM |
| Example 16 | 0.2 μM | 100 μM |
| Example 19 | 0.1 μM | 100 μM |
| Example 53 | 0.15 μM | 100 μM |
| Example 56 | 0.75 μM | 100 μM |
| Example 58 | 0.15 μM | 20 μM |

What is claimed is:

1. A method for the treatment of restenosis in a mammal said method comprising administering a therapeutically effective amount of a compound of formula (I):

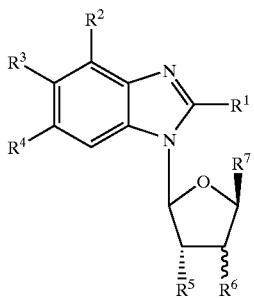
(I)

wherein $R^1$ represents hydrogen, a halo atom, azido,

—$NR^8R^9$ where $R^8$ and $R^9$ are the same or different and are each independently selected from the group consisting of hydrogen, hydroxyl, $C_{1-12}$ alkyl where the alkyl moiety is optionally substituted by one or more substituents selected from the group consisting of halo, amino, azido, hydroxy, cyano, $NO_2$, $NHR^{10}$, $SO_2R^{10}$, $SR^{10}$, $OR^{10}$, $COR^{10}$ and haloC$_{1-8}$ alkyl where $R^{10}$ is $C_{1-6}$ alkyl, $C_{3-6}$ alkenyl, $C_{2-6}$ alkynyl, or aryl, $C_{2-8}$ alkenyl, $C_{1-6}$ alkoxy, $C_{3-7}$ cycloalkyl, $C_{2-8}$ alkynyl, $C_{3-7}$ cycloalkenyl, $C_{3-7}$ cycloalkylC$_{1-5}$ alkyl, aryl, arylC$_{1-6}$ alkyl, heteroaryl, heteroarylC$_{1-6}$ alkyl, heterocyclyl and heterocyclylC$_{1-6}$ alkyl or $R^8R^9$ together with the N atom to which they are attached form a 3,4,5 or 6 membered heterocyclic ring;

—$NHNR^{11}R^{12}$ where $R^{11}$ and $R^{12}$ are the same or different and each represent hydrogen or $C_{1-6}$ alkyl;

—N=NC$_{1-6}$ alkyl or —NHOC$_{1-6}$ alkyl;

$R^2$ represents hydrogen, halo atom, $C_{1-6}$ alkyl or $C_{2-6}$ alkenyl;

$R^3$ and $R^4$ are the same or different and each represent hydrogen, halogen or $NO_2$;

wherein the sugar moiety of Formula I is selected from the group consisting of:

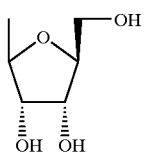
a

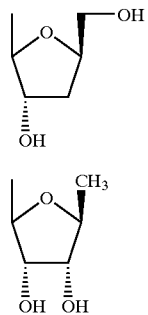
b c d e f with the proviso that when $R^2$ represents hydrogen, $R^3$ and $R^4$ each represent chloro, and the sugar moiety is a then $R^1$ represents:

azido,

—$NR^8R^9$ where $R^8$ and $R^9$ are the same or different and are each independently selected from the group consisting of hydroxyl, $C_{1-6}$ alkyl, where the alkyl moiety is substituted by one or more substituents selected from the group consisting of amino, azido, $NO_2$, $NHR^{10}$, $SO_2R^{10}$, $SO_2R^{10}$, $OR^{10}$, haloC$_{1-6}$ alkyl where $R^{10}$ is as hereinbefore defined, $C_{7-12}$ alkyl, where the alkyl moiety is optionally substituted by one or more substituents selected from the group consisting of halo, amino, azido, hydroxy, cyano, $NO_2$, $NHR^{10}$, $SO_2R^{10}$, $SR^{10}$, $OR^{10}$, $COR^{10}$ and haloC$_{1-6}$ alkyl where $R^{10}$ is as herein before defined, $C_{1-6}$ alkoxy, $C_{3-7}$ cycloalkenyl, heteroaryl, heteroaryl $C_{1-6}$ alkyl and heterocyclyl;

—$NHNR^{11}R^{12}$ where $R^{11}$ and $R^{12}$ are as hereinbefore defined;

—N=NC$_{1-6}$ alkyl or

—NHOC$_{1-6}$ alkyl;

or a pharmaceutically acceptable derivative thereof.

2. The method according to claim 1, wherein the compound of formula (I) is defined where $R^1$ is —$NR^8R^9$ where $R^8$ is hydrogen and $R^9$ is $C_{1-6}$ alkyl, $R^2$ is hydrogen or a halo atom, $R^3$ and $R^4$ are both a halo atom and the sugar moiety is selected from the group consisting of 3'-deoxy-L-ribofuranosyl, 5'-deoxy-L-ribofuranosyl and 2'-deoxy-L-ribofuranosyl or a pharmaceutically acceptable derivative thereof.

3. The method according to claim 1, wherein the compound of formula (I) is selected from the group consisting of:
- 4-Bromo-5,6-dichloro-2-isopropylamino-1-(beta-L-ribofuranosyl)-1H-benzimidazole;
- 5,6-Dichloro-1-(3-deoxy-beta-L-ribofuranosyl)-2-isopropylamino-1H-benzimidazole;
- 5,6-Dichloro-1-(5-deoxy-beta-L-ribofuranosyl)-2-isopropylamino-1H-benzimidazole;
- 5,6-Dichloro-1-(beta-L-erythrofuranosyl)-2-isopropylamino-1H-benzimidazole;
- 5,6-Dichloro-2-isopropylamino-1-(beta-L-xylofuranosyl)-1H-benzimidazole;
- 1-(2-Deoxy-beta-L-ribofuranosyl)-5,6-dichloro-2-isopropylamino-1H-benzimidazole;
- 2-Isopropylamino-1-(beta-L-ribofuranosyl)-4,5,6-trichloro-1H-benzimidazole;
- 4-Bromo-2-cylopropylamino-5,6-dichloro-1-(beta-L-ribofuranosyl)-1H-benzimidazole;
- 2-Cylopropylamino-1-(beta-L-ribofuranosyl)-4,5,6-trichloro-1H-benzimidazole;
- 4,6-Dichloro-2-isopropylamino-1-(beta-L-ribofuranosyl)-1H-benzimidazole; and
- 1-(beta-L-Erythrofuranosyl)-2-isopropylamino-4,5,6-trichloro-1H-benzimidazole.

4. A method for the treatment of restenosis following angloplasty in a mammal, said method comprising administering a therapeutically effective amount of a compound of formula (I):

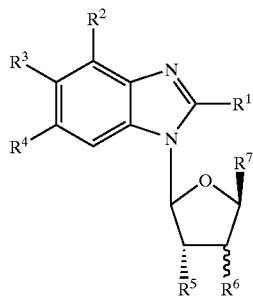

(I)

wherein
$R^1$ represents hydrogen, a halo atom, azido,
—$NR^8R^9$ where $R^8$ and $R^9$ are the same or different and are each independently selected from the group consisting of hydrogen, hydroxyl, $C_{1-2}$ alkyl where the alkyl moiety is optionally substituted by one or more substituents selected from the group consisting of halo, amino, azido, hydroxy, cyano, $NO_2$, $NHR^{10}$, $SO_2R^{10}$, $SR_2O^{10}$, $OR^{10}$, $COR^{10}$ and haloC$_{1-6}$ alkyl where $R^{10}$ is $C_{1-6}$ alkyl, $C_{3-5}$ alkenyl, $C_{2-6}$ alkynyl, or aryl, $C_{2-8}$ alkenyl, $C_{1-6}$ alkoxy, $C_{3-7}$ cycloalkyl, $C_{2-8}$ alkynyl, $C_{3-7}$ cycloalkenyl, $C_{3-7}$ cycloalkylC$_{1-6}$ alkyl, aryl, arylC$_{1-6}$ alkyl, heteroaryl, heterocarylC$_{1-6}$ alkyl, heterocyclyl and heterocyclylC$_{1-6}$ alkyl or $R^8R^9$ together with the N atom to which they are attached form a 3,4,5 or 6 membered heterocyclic ring;

—$NHNR^{11}R^{12}$ where $R^{11}$ and $R^{12}$ are the same or different and each represent hydrogen or $C_{1-6}$ alkyl;
—$N=NC_{1-6}$ alkyl or —$NHOC_{1-6}$ alkyl;
$R^2$ represents hydrogen, halo atom, $C_{1-6}$ alkyl or $C_{2-6}$ alkenyl;
$R^3$ and $R^4$ are the same or different and each represent hydrogen, halogen or $NO_2$;
wherein the sugar moiety of Formula I is selected from the group consisting of:

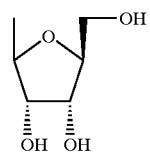

a

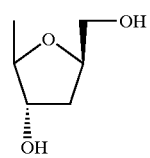

b

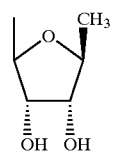

c

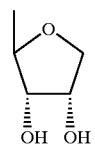

d

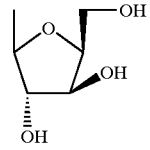

e

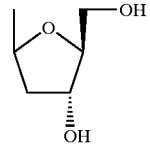

f with the proviso that when $R^2$ represents hydrogen, $R^3$ and $R^4$ each represent chloro, and the sugar moiety is

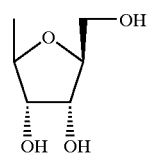

a then $R^1$ represents:
azido,
—$NR^8R^9$ where $R^8$ and $R^9$ are the same or different and are each independently selected from the group consisting of hydroxyl, $C_{1-6}$ alkyl, where the alkyl moiety is substituted by one or more substituents selected from the group consisting of amino, azido, $NO_2$, $NHR^{10}$, $SO_2R^{10}$, $SR^{10}$, $OR^{10}$, halo$C_{1-6}$ alkyl where $R^{10}$ is as hereinbefore defined, $C_{7-12}$ alkyl, where the alkyl moiety is optionally substituted by one or more substituents selected from the group consisting of halo, amino, azido, hydroxy, cyano, $NO_2$, $NHR^{10}$, $SO_2R^{10}$, $SR^{10}$, $OR^{10}$, $COR^{10}$ and halo$C_{1-6}$ alkyl where $R^{10}$ is as hereinbefore defined, $C_{1-6}$ alkoxy, $C_{3-7}$ cycloalkenyl, heteroaryl, heteroaryl $C_{1-6}$ alkyl and heterocyclyl;

—$NHNR^{11}R^{12}$ where $R^{11}$ and $R^{12}$ are as hereinbefore defined;

—N=N$C_{1-6}$ alkyl or

—NHO$C_{1-6}$ alkyl;

or a pharmaceutically acceptable derivative thereof.

5. The method according to claim 4, wherein the compound of formula (I) is selected from the group consisting of:

4-Bromo-5,6-dichloro-2-isopropylamino-1-(beta-L-ribofuranosyl)-1H-benzimidazole;

5,6-Dichloro-1-(3-deoxy-beta-L-ribofuranosyl)-2-isopropylamino-1H-benzimidazole;

5,6-Dichloro-1-(5-deoxy-beta-L-ribofuranosyl)-2-isopropylamino-1H-benzimidazole;

5,6-Dichloro-1-(beta-L-erythrofuranosyl)-2-isopropylamino-1H-benzimidazole;

5,6-Dichloro-2-isopropylamino-1-(beta-L-xylofuranosyl)-1H-benzimidazole;

(2-Deoxy-beta-L-ribofuranosyl)-5,6-dichloro-2-isopropylamino-1H-benzimidazole;

2-Isopropylamino-1-(beta-L-ribofuranosyl)-4,5,6-trichloro-1H-benzimidazole;

4-Bromo-2-cylopropylamino-5,6-dichloro-1-(beta-L-ribofuranosyl)-1H-benzimidazole;

2-Cylopropylamino-1-(beta-L-ribofuranosyl)-4,5,6-trichloro-1H-benzimidazole;

4,6-Dichloro-2-isopropylamino-1-(beta-L-ribofuranosyl)-1H-benzimidazole; and 1-(beta-L-Erythrofuranosyl)-2-isopropylarmino-4,5,6-trichloro-1H-benzimidazole.

* * * * *

UNITED STATES PATENT AND TRADEMARK OFFICE
CERTIFICATE OF CORRECTION

PATENT NO. : 6,617,315 B1
DATED : September 9, 2003
INVENTOR(S) : Chamberlain et al.

It is certified that error appears in the above-identified patent and that said Letters Patent is hereby corrected as shown below:

Column 37,
Line 41, reads "$SR^{10}$, $OR^{10}$, $COR^{10}$ and halo$C_{1-8}$ alkyl where $R^{10}$ is" should read
-- $SR^{10}$, $OR^{10}$, $COR^{10}$ and halo$C_{1-6}$ alkyl where $R^{10}$ is --
Line 44, reads "cycloalkenyl, $C_{3-7}$ cycloalkyl$C_{1-5}$ alkyl, aryl aryl$C_{1-6}$" should read
-- cycloalkenyl, $C_{3-7}$ cycloalkyl$C_{1-6}$ alkyl, aryl aryl$C_{1-6}$ --

Column 38,
Line 52, reads "$NO_2$, $NHR^{10}$, $SO_2R^{10}$, $SO_2R^{10}$, $OR^{10}$, halo$C_{1-6}$ alkyl" should read
-- $NO_2$, $NHR^{10}$, $SO_2R^{10}$, $SR^{10}$, $OR^{10}$, halo$C_{1-6}$ alkyl --

Column 39,
Line 35, reads "angloplasty in a mammal, said method comprising admin-" should read
-- angioplasty in a mammal, said method comprising admin- --
Line 56, reads "sisting of hydrogen, hydroxyl, $C_{1-2}$ alkyl where the" should read
-- sisting of hydrogen, hydroxyl, $C_{1-12}$ alkyl where the --
Line 60, reads "$SR_2O^{10}$, $OR^{10}$, $COR^{10}$ and halo$C_{1-6}$ alkyl where $R^{10}$ is" should read
-- $SR^{10}$, $OR^{10}$, $COR^{10}$ and halo$C_{1-6}$ alkyl where $R^{10}$ is --
Line 61, reads "$C_{1-6}$ alkyl, $C_{3-5}$ alkenyl, $C_{2-6}$ alkynyl, or aryl, $C_{2-6}$" should read
-- $C_{1-6}$ alkyl, $C_{3-6}$ alkenyl, $C_{2-6}$ alkynyl, or aryl, $C_{2-6}$ --
Line 64, reads "alkyl, heteroaryl, heterocaryl$C_{1-6}$ alkyl, heterocyclyl" should read
-- alkyl, heteroaryl, heteroaryl$C_{1-6}$ alkyl, heterocyclyl --

Signed and Sealed this

Thirteenth Day of January, 2004

JON W. DUDAS
*Acting Director of the United States Patent and Trademark Office*